United States Patent [19]

Riess et al.

[11] Patent Number: 5,344,930
[45] Date of Patent: Sep. 6, 1994

[54] FLUORINE AND PHOSPHOROUS-CONTAINING AMPHIPHILIC MOLECULES WITH SURFACTANT PROPERTIES

[75] Inventors: Jean G. Riess, Falicon; Francois Jeanneaux, Nice; Marie-Pierre Krafft, Nice; Catherine Santaella, Nice; Pierre Vierling, Falicon, all of France

[73] Assignee: Alliance Pharmaceutical Corp., San Diego, Calif.

[21] Appl. No.: 149,008

[22] Filed: Nov. 8, 1993

Related U.S. Application Data

[63] Continuation of Ser. No. 542,227, Jun. 22, 1990, abandoned.

[51] Int. Cl.$^5$ .......... C07F 9/6533; C07F 9/24; C07F 9/10; C07F 9/59; C07F 9/572; C07F 9/568; C07F 9/564; C07F 9/14
[52] U.S. Cl. .......... 544/84; 546/21; 548/412; 548/950; 548/956; 558/166; 558/169; 558/170; 558/171; 558/173; 558/174; 558/177; 558/179; 558/180; 558/182; 558/183; 558/185; 558/186; 558/188; 558/202; 558/204
[58] Field of Search .......... 544/84; 558/169, 177, 558/180, 186

[56] References Cited

U.S. PATENT DOCUMENTS

| | | | |
|---|---|---|---|
| 3,692,885 | 9/1972 | Anello et al. | 558/177 X |
| 3,948,887 | 4/1976 | Hager. | |
| 3,976,698 | 8/1976 | Hager. | |
| 4,034,022 | 7/1977 | Demarcq et al. | |
| 4,736,051 | 5/1988 | Wakatsuki et al. | |
| 4,740,609 | 5/1988 | Wakatsuki et al. | |

FOREIGN PATENT DOCUMENTS

| | | |
|---|---|---|
| 2405042 | 8/1975 | Fed. Rep. of Germany. |
| 0222595 | 5/1985 | Fed. Rep. of Germany. |
| 61-123590 | 6/1986 | Japan. |
| 61-123591 | 6/1986 | Japan. |
| 0492741 | 6/1970 | Switzerland. |
| 2172889 | 10/1986 | United Kingdom. |

OTHER PUBLICATIONS

Chem. Abstr. 104, 207612 (JP 60-181093 publ. 14-Sep.-85).
Chem. Abstr. 110, 115118b (JP 63-208593 publ. 30-Aug.-88).
Fujita et al. *Chem. Pharm Bull.* 35:647 (1987).
Gu et al., *Chem. Abstr.* 110(17); p. 117, 154749c (24 Apr. 1989) citing *Acta Chimica Sinica* 46(9)):913 (1988).
Kinitake et al. *Memoirs of the Faculty of Engineering, Kyushu University* 46:221 (1986).
Mahmood et al., *Inorg. Chem.* 25:4081 (1986).

*Primary Examiner*—Robert W. Ramsuer
*Assistant Examiner*—Michael G. Anbrose
*Attorney, Agent, or Firm*—Knobbe, Martens, Olson & Bear

[57] ABSTRACT

Compounds of the general formula:

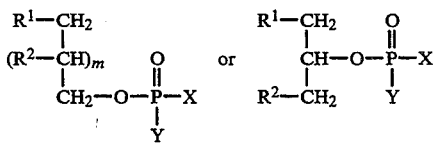

are useful as surfactants in the preparation of fluorocarbon emulsions, which can be used as oxygen-carrying blood substitutes, and for many other therapeutic and diagnostic applications. They are further useful in liposomal formulations which are themselves therapeutic agents or provide a vehicle for such agents.

13 Claims, 10 Drawing Sheets

FIG. IA
COMPOUNDS
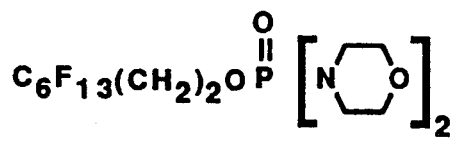
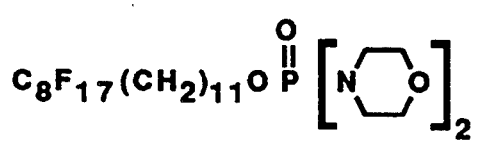
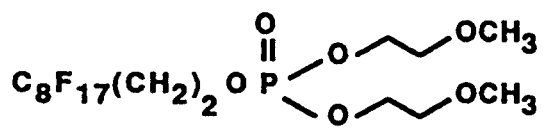
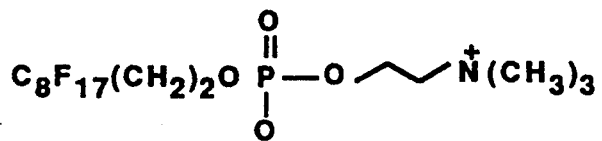
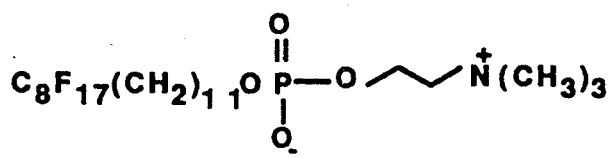
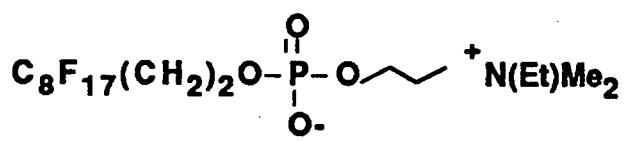
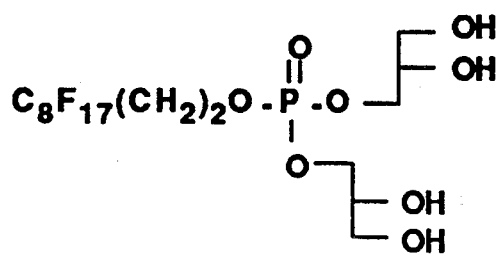

COMPOUNDS

FLUORINE AND PHOSPHOROUS-CONTAINING AMPHIPHILIC MOLECULES WITH SURFACTANT PROPERTIES

This application is a continuation of application Ser. No. 07/542,227, filed Jun. 22, 1990 abandoned.

BACKGROUND OF THE INVENTION

This invention relates to surfactants which as amphiphitic molecules have a variety of applications, in particular in the preparation of liposomes, dispersions, and emulsions such as fluorocarbon emulsions.

The achievement of an intravenously injectable oxygen-delivering system has become a major objective in biomedical research. Such a system is destined to serve as a temporary substitute for blood, but also, more generally, whenever in vivo administration of oxygen is required, as for example in cases of myocardial infarction or stroke, during cardiovascular surgery, for the preservation of isolated tissues and organs, as an adjuvant to cancer radio- and chemo- therapy and in perioperative hemodilution. Fluorocarbons presently appear to be the most promising oxygen vectors for this purpose. Fluorocarbons also have significant utility as contrast enhancement agents, such as for diagnosis by X-ray, magnetic resonance or ultrasound radiography.

The intravenous injection of neat fluorocarbons is, however, precluded by their insolubility in an aqueous medium. It is therefore necessary to prepare them in the form of emulsions, which implies the use of one or more surfactants. Although albumin has been used as a surfactant, the primary synthetic surfactants used in fluorocarbon emulsions today are polyoxyethylene polyoxypropylene block co-polymers of PLURONIC F-68 type, and natural surfactants such as egg-yolk lecithins.

Lecithins, however, have their drawbacks and limitations; they are sensitive, oxidizable materials; reliable sources of consistent quality are few; they are not particularly fluorophilic; and they leave little room for manipulating the emulsions' characteristics in order to adjust them to specific therapeutic applications.

Further mastery of the art of fluorocarbon emulsion technology is desirable, especially to allow the optimal adaptation of the emulsions characteristics to each individual therapeutic application and to extend their spectrum of application. A further, ideal, objective would be the ability to modulate the biological response they trigger in the organism.

Likewise it is desirable to gain further mastery in the art of liposome technology, especially to allow the modulation of the characteristics and properties of lipid membranes and liposomes and to extend their spectrum of applications, especially for drug and contrast agent delivery.

The present invention provides various fluorine-substituted lecithin analogues and derivatives, which are useful as surfactants in fluorocarbon emulsions and in lipid membranes and in liposome manufacturing.

Certain fluorine-containing surfactants are known. For example, DE-A-2160783 discloses certain fluorocarbon phosphoric acid derivatives having a chlorine atom substituted on the carbon atom $\beta$- to the phosphate group.

Fujita et al. (JP-A-60181093, Chem. Pharm. Bull., 35:647 (1987) disclose certain fluorocarbon phosphoric acid derivatives based on glycerol in which a single fluorine-containing ($R_F$) moiety is present and the secondary alcohol function is either free (OH) or acetylated ($OCOCH_3$). DD-A222595 discloses some fluorinated glycerophosphocholine derivatives bun these contain only a 2,2,2-trifluoroethyl group.

The article by Gu et al [Chemical Abstract 110:154749c (1989); HUAXUE XUEBAO or Acta Chimica Sinica, 49:913 (1988)], discloses phosphatidylcholine derivatives having two F-alkyl chains, but these contain a chlorine atom at their extremity.

Kunitake et al (Memoirs of the Faculty of Engineering, Kyushu University 46 221 (1986)) disclose fluorocarbon phosphoric acid derivatives which contain an amide linkage, as a result of being a glutamic acid diester.

DE-A-2656429 discloses certain fluorocarbon phosphorous (not phosphoric) acid derivatives including the presence of a CH=CF double bond.

Various publications also disclose one or two fluorocarbon moieties substituted onto a phosphoric acid moiety; in the case of the mono-substituted compounds both remaining groups of the phosphoric acid are independently hydroxy, alkoxy, alkylthio or alkylamino.

DE-A-3609491, DE-A-3609492 and JP-A-84204197 disclose certain dibasic fluorocarbon-substituted phosphoric acid derivatives.

JP-A-8623590 and JP-A-86123591 (Fuji) disclose certain fluorocarbon-substituted phosphoric acid derivatives having no methylene groups.

Mahmood et al (Inorg. Chem. 25 4081 (1986)) discloses molecules having central bifunctional fluorinated chains with two phosphate groups, one on each end of the chain.

Various sulphonamides containing fluorocarbon moieties and a phosphoric acid residue are known.

U.S. Pat. No. 3976698 and U.S. Pat. No. 3948887 (Pennwalt) disclose certain sulphur-containing fluorocarbon-substituted phosphoric acid derivatives.

None of the above documents discloses the use of the surfactants disclosed in fluorocarbon emulsions. Further, none of the prior documents discloses compounds within the scope of the present invention.

SUMMARY OF THE INVENTION

The invention is directed toward novel surfactants having the general formula

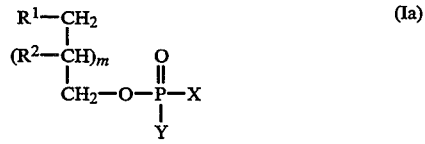

(Ia)

or

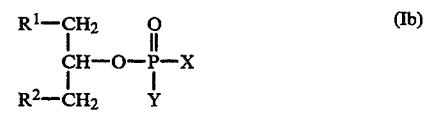

(Ib)

wherein $R^1$ and $R^2$ are fluorine containing moieties, and X and Y substituents are as defined herein.

The invention is also directed to methods of using the novel compounds described. The amphiphilic nature of the molecules combined with their biocompatibility make them useful in the preparation of emulsions and liposomal formulations which can be adapted to many biological and medical applications.

Finally, methods of preparing the compounds of Formula I are provided herein.

BRIEF DESCRIPTION OF THE DRAWINGS

The description makes reference to the accompanying drawings, in which.

DETAILED DESCRIPTION OF THE INVENTION

Figure 1:
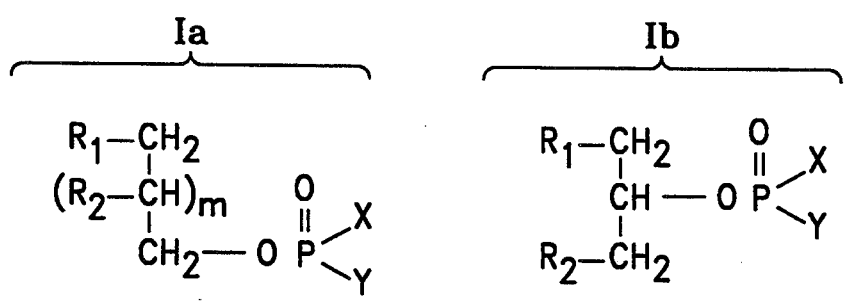
FIG. 1 shows the structures of preferred compounds of the invention.
Figure 1B:
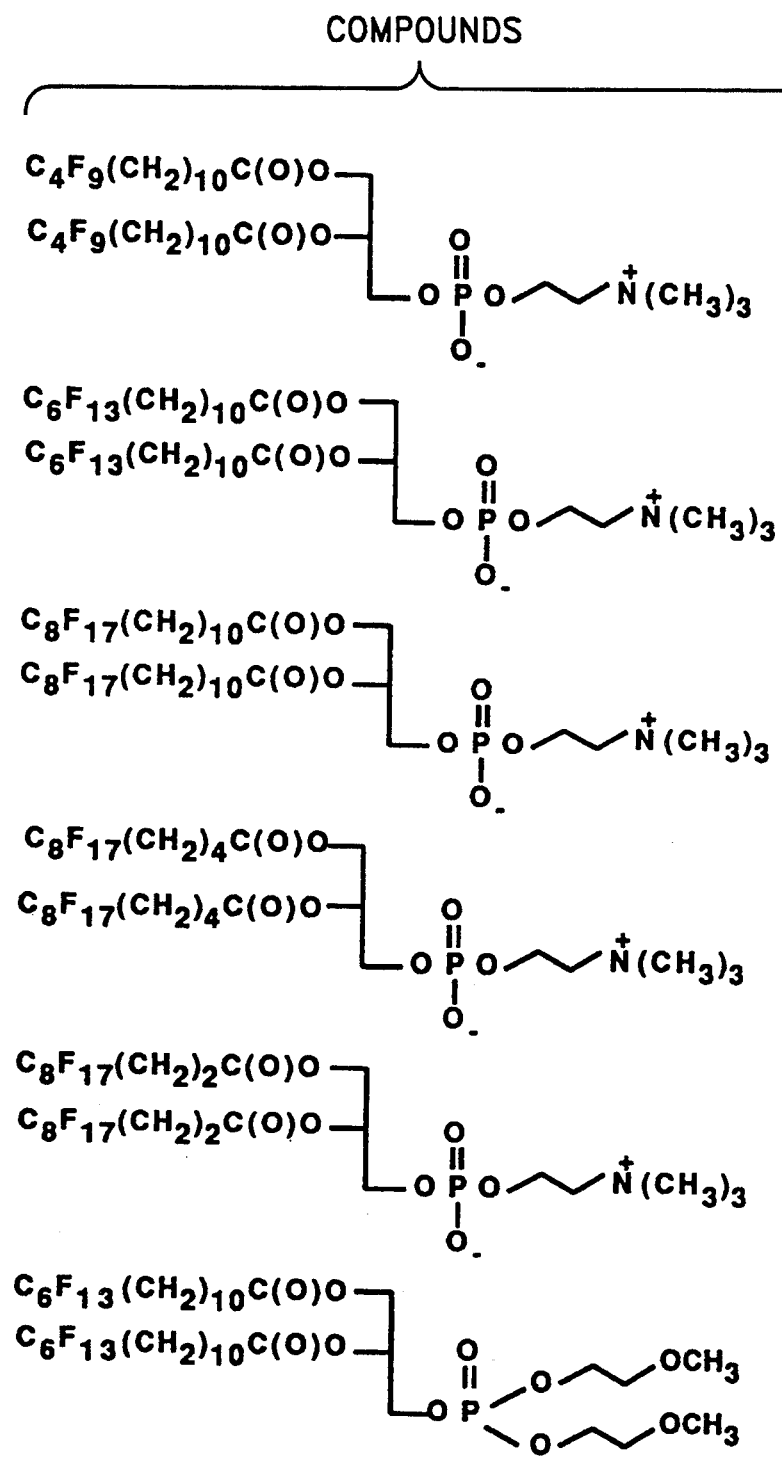
Figure 1C:
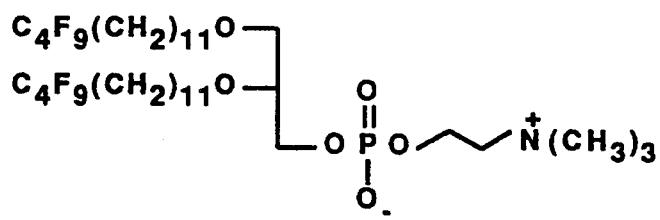
Figure 1C:
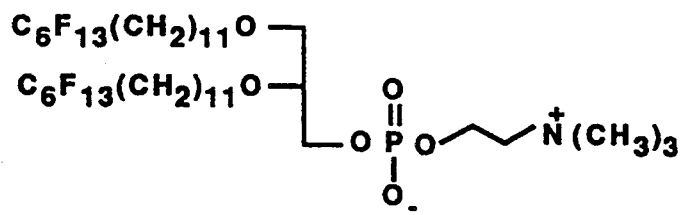
Figure 1C:
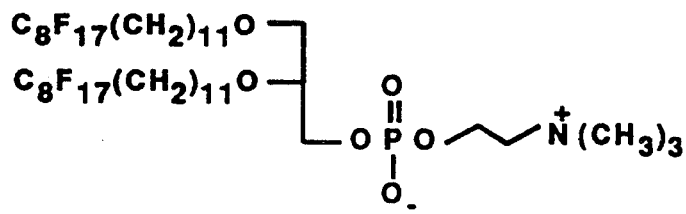
Figure 1C:
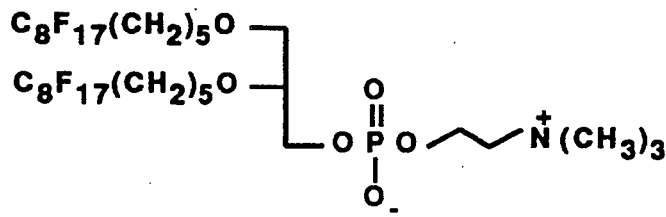
Figure 1C:
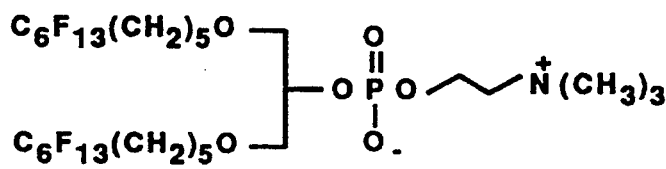
Figure 1C:
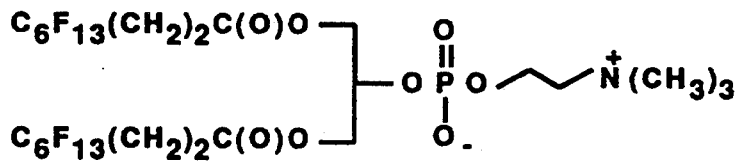
Figure 1C:
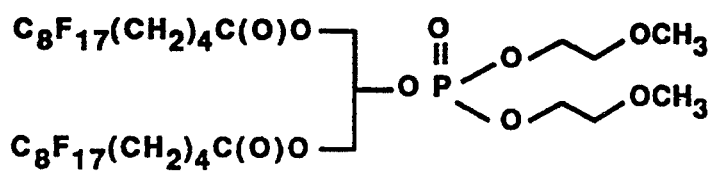

According to a first aspect of the invention, there is provided a compound of the general formula:

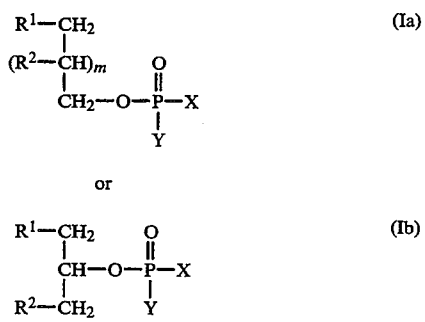

wherein:

$R^1$ represents:

$R_F(CH_2)_a$—$(CH=CH)_b$—$(CH_2)_c$—$(CH=CH)_d$—$(CH_2)_e$—A—;

$R_F$—$(CH_2)_f$—$OCH_2CH(CH_2OH)CH_2$—A—;

$R_F$—$(CH_2)_g$—$OCH_2CH(CH_2OH)$—A—, wherein —A— represents —O—, —C(O)O—, —$R^6(R^7)N^+$—, (wherein each of $R^6$ and $R^7$ represents $C_1$-$C_4$ alkyl or hydroxyethyl), —$(CH_2)_n$—, wherein n+0 or 1, or —C(O)N($R^9$)—$(CH_2)_q$—B, wherein q is an integer from 0 to 12, B represents —O— or —C(O)—, and $R^9$ is hydrogen or $R^6$, and wherein the sum of a+c+e is from 0 to 11, the sum b+d is from 0 to 12 and each of f and g is from 1 to 12;

$R_F$—$(CH_2$—$CH_2$—$O)_h$—;

$R_F$—$[CH(CH_3)CH_2O]_h$—;

$R_F(—CH_2$—$CH_2$—$S)_h$—, wherein h is from 1 to 12; and wherein $R_F$ represents a fluorine-containing moiety having one of the following structures:

(a) $F(CF_2)_i$—, wherein i is from 2 to 12, (b) $(CF_3)_2CF(CF_2)_j$—, wherein j is from 0 to 8, (c) $R_{F}1[CF_2CF(CF_3)]_k$—, wherein k is from 1 to 4, and $R_{F}1$ represents $CF_3$—, $C_2F_5$— or $(CF_3)_2CF$—, (d) $R_{F}2(R_{F}3)CFO(CF_2CF_2)_l$—, wherein l is from 1 to 6 and wherein each of $R_{F}2$ and $R_{F}3$ independently represents $C_F3$—, $C_2F_5$—, n—$C_3F_7$— or $CF_3CF_2CF(CF_3)$—, or $R_{F}2$ and $R_{F}3$ taken together represent —$(CF_2)_4$— or —$(CF_2)_5$—, or (e) one of the structures (a) to (d) in which one or more of the fluorine atoms are replaced by one or more hydrogen or bromine atoms and/or at least two chlorine atoms in a proportion such that at least 50% of the atoms bonded to the carbon skeleton of $R_F$ are fluorine atoms, and wherein $R_F$ contains at least 4 fluorine atoms;

m is 0 or 1;

$R^2$ represents $R^1$, hydrogen or a group OR, wherein R represents a saturated or unsaturated $C_1$-$C_{20}$ alkyl (preferably $C_1$-$C_8$ alkyl) or $C_3$-$C_{20}$ acyl (preferably $C_3$-$C_8$ acyl); and when m is 1, $R^1$ and $R^2$ may exchange their positions; and each of X and Y independently represent: hydroxyl; —$O(CH_2CH_2O)_nR^3$, wherein n is an integer from 1 to 5 and $R^3$ represents a hydrogen atom or $C_1$-$C_4$ alkyl group;

—$OCH_2CH(OH)CH_2OH$;

—$NR^4R^5$ or $N^+R^4R^5R^8$, wherein each of $R^4$, $R^5$ and $R^8$ independently represents a hydrogen atom, a $C_1$-$C_4$ alkyl group, —$CH_2CH_2O(CH_2CH_2O)_sR^3$, wherein s represents an integer of from 1 to 5, or $R^4$ and $R^5$ when taken together represent —$(CH_2)_q$ where q is an integer of from 2 to 5, or with the nitrogen atom $R^4$ and $R^5$ form a morpholino group;

—$O(CH_2)_pZ$ wherein Z represents a 2-aminoacetic acid group, —$NR^4R^5$ or —$NR^4R^5R^8$ where $R^8$ is as defined for $R^4$ and $R^5$ above, and p is an integer of from 1 to 5;

with the proviso that X and Y do not both represent hydroxyl or an ionized form derived from hydroxyl.

It is to be appreciated that at least some of the compounds of general formulae Ia and Ib can exist in ionized or non-ionized form. The exact nature of the species present will of course depend on the environment and in particular the pH.

For a better understanding of the invention, and to show how it may be put into effect, preferred embodiments of the invention, in its first and other aspects, will now be described.

Preferred compounds of general formulae Ia and Ib have, independently or (where compatible) together, one or more of the following characteristics:

in general formula Ia, m=0;

in general formula Ia, m=1;

$R^2$ represents $R^1$;

$R^1$ represents a group $R_F(CH_2)_a$—$(CH=CH)_b$—$(CH_2)_c$—$(CH=CH)_d$—$(CH_2)_e$—A—;

preferably b+d=0.

preferably —A— represents —O—, —C(O)O—, or

—$(CH_2)_n$—(wherein n=0);

$R_F$ represents any of the previously defined structures (a) to (d), where one or more of the fluorine atoms are replaced by one or more hydrogen or bromine atoms;

$R_F$ represents $F(CF_2)_i$—, wherein i is from 2 to 12; preferably $R_F$ represents $F(CF_2)_i$—, wherein i is from 4 to 8;

each of X and Y independently represents hydroxyl, morpholino, a group $OCH_2CH(OH)CH_2)OH$, or a group $O(CH_2CH_2O)_nR^3$, wherein n is 1 or 2 and $R^3$ represents methyl; and each of X and Y independently represents —O(CH$_2$)$_p$Z where p is an integer from 1 to 5, and preferably 2, and Z represents —NR$^4$R$^5$ or NR$^4$R$^5$R$^8$ where each of R$^4$, R$^5$ and R$^8$ represents a methyl or an ethyl group;

with the proviso that X and Y do not both represent hydroxyl or an ionized from derived from hydroxyl.

Particularly preferred compounds in accordance with the invention are shown in FIG. 1.

Compounds in accordance with the first aspect may be prepared by any convenient method. Certain methods of preparing such compounds however will be preferred as a matter of practice.

Figure 2A:
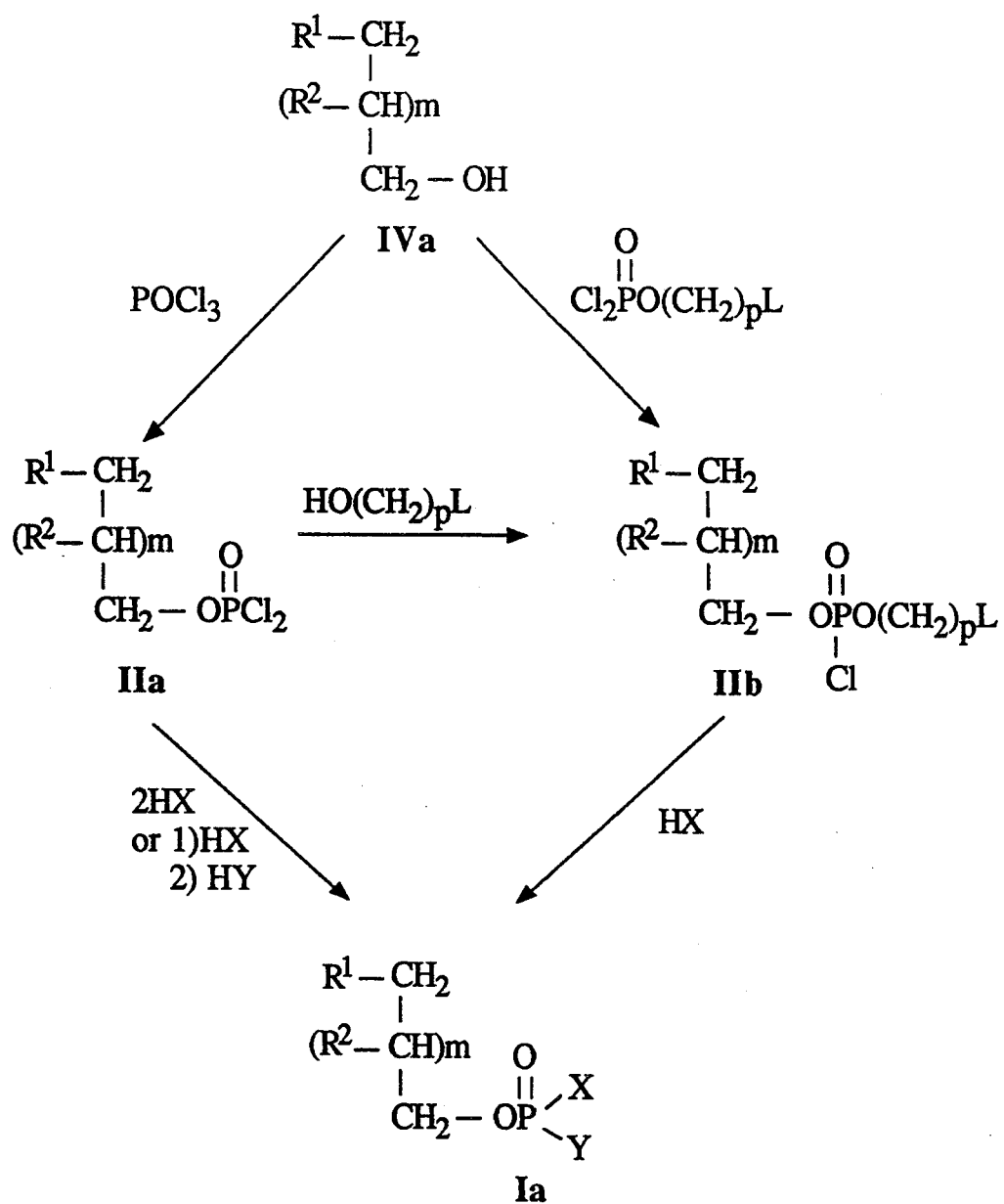
FIG. 2 shows a general synthetic scheme for preparing compounds of general formulae Ia and Ib and certain intermediate compounds.
Figure 2B:
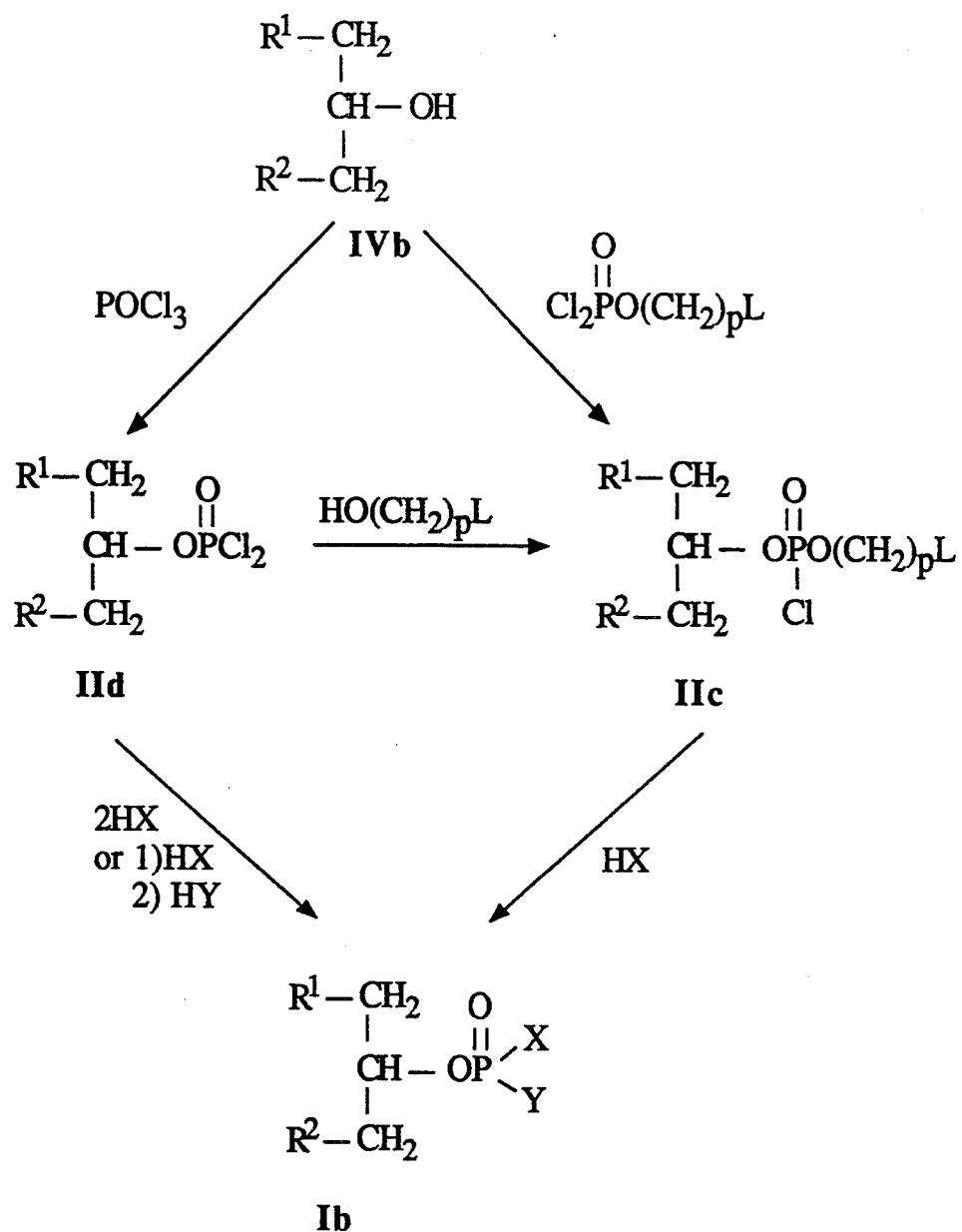

According to a second aspect of the present invention, there is provided a process for the preparation of a compound in accordance with the first aspect, the process comprising:

(a) reacting a compound of general formula IIa, IIb, IIc, or IId, as shown in FIG. 2, with a compound HX to effect mono-substitution, and in the case of IIa and IIb, working up the mono-chlorinated product to a mono-hydroxylated product, and optionally allowing the product to react with the HY to effect di-substitution; or (b) when X and/or Y represents a group —O(CH$_2$)$_p$Z, wherein p is an integer from 1 to 5 and Z represents a group NR$^4$R$^5$ or N$^+$R$^4$R$^5$R$^8$, reacting a compound of general formula IIb or IIc, as shown in FIG. 2, wherein L represents Z or a leaving group, and when L is Z with HX, and when L is a leaving group with HX, then with a compound HNR$^4$R$^5$, HN$^+$R$^4$R$^5$R$^8$, or NR$^4$R$^5$R$^8$, to effect mono- or di-substitution and in the case of mono-substitution of a compound of general formula IIb or IIc working up the mono-chlorinated product to a mono-hydroxylated product;

(c) optionally after step (a) or (b) converting a compound of general formula Ia or Ib so formed into another compound of general formula Ia or Ib.

Compounds of general formulae IIb and IIc may be prepared from compounds of general formulae IIa and IId respectively, as shown in FIG. 2, by reaction with a compound of the general formula HO(CH$_2$)$_p$L, wherein p is defined as for general formulae Ia an Ib and L represents Z, or a leaving group, for example a halogen atom such as bromine.

Compounds of general formulae IIb and IIc may also be prepared from compounds of the formulae IVa and IVb respectively by reaction with a compound of the general formula Hal$_2$P(O)O(CH$_2$)$_p$L, where p is as defined for formulae Ia and Ib, L represents Z or a leaving group as before and Hal represents a halogen atom such as chlorine, which is either available in the art or may be synthesized by methods known to those skilled in the art.

Compounds of general formulae IIa and IId can be prepared from compounds of general formulae IVa and IVb, respectively, as shown in FIG. 2, by reaction with phosphorus oxychloride (POCl$_3$). Compounds of general formulae IVa and IVb and the other reagents used are either available in the art or may be synthesized by methods known to those skilled in the art.

Compounds of general formulae IIa, IIb, IIc, and IId are valuable intermediates in the preparation of compounds of general formulae Ia and Ib. According to a third aspect of the present invention there is provided a compound of general formula IIa or IId; according to a fourth aspect there is provided a compound of general formula IIb or IIc.

Figure 3A:
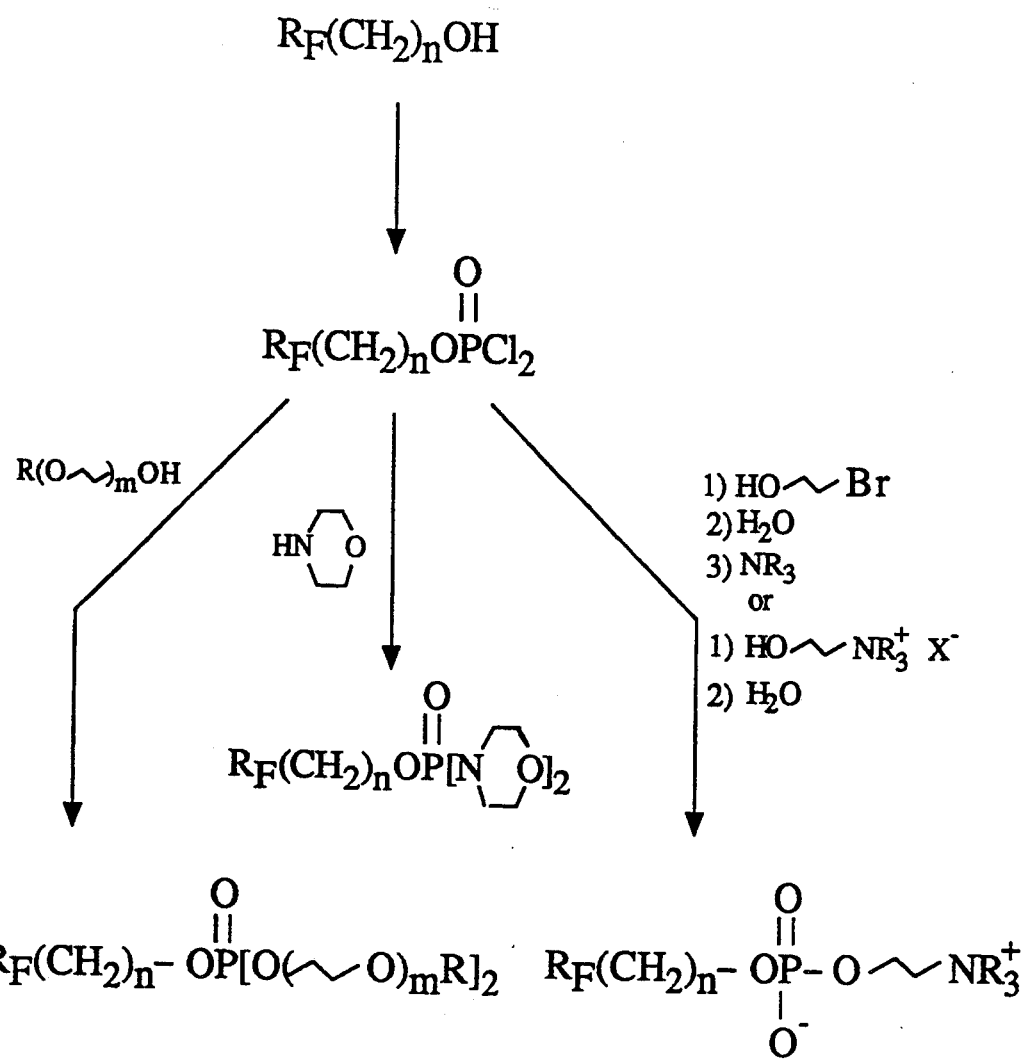
FIG. 3 shows an exemplary synthetic scheme for preparing certain compounds of the invention, which may be extended by analogy for the preparation of other compounds of the invention.
Figure 3B:
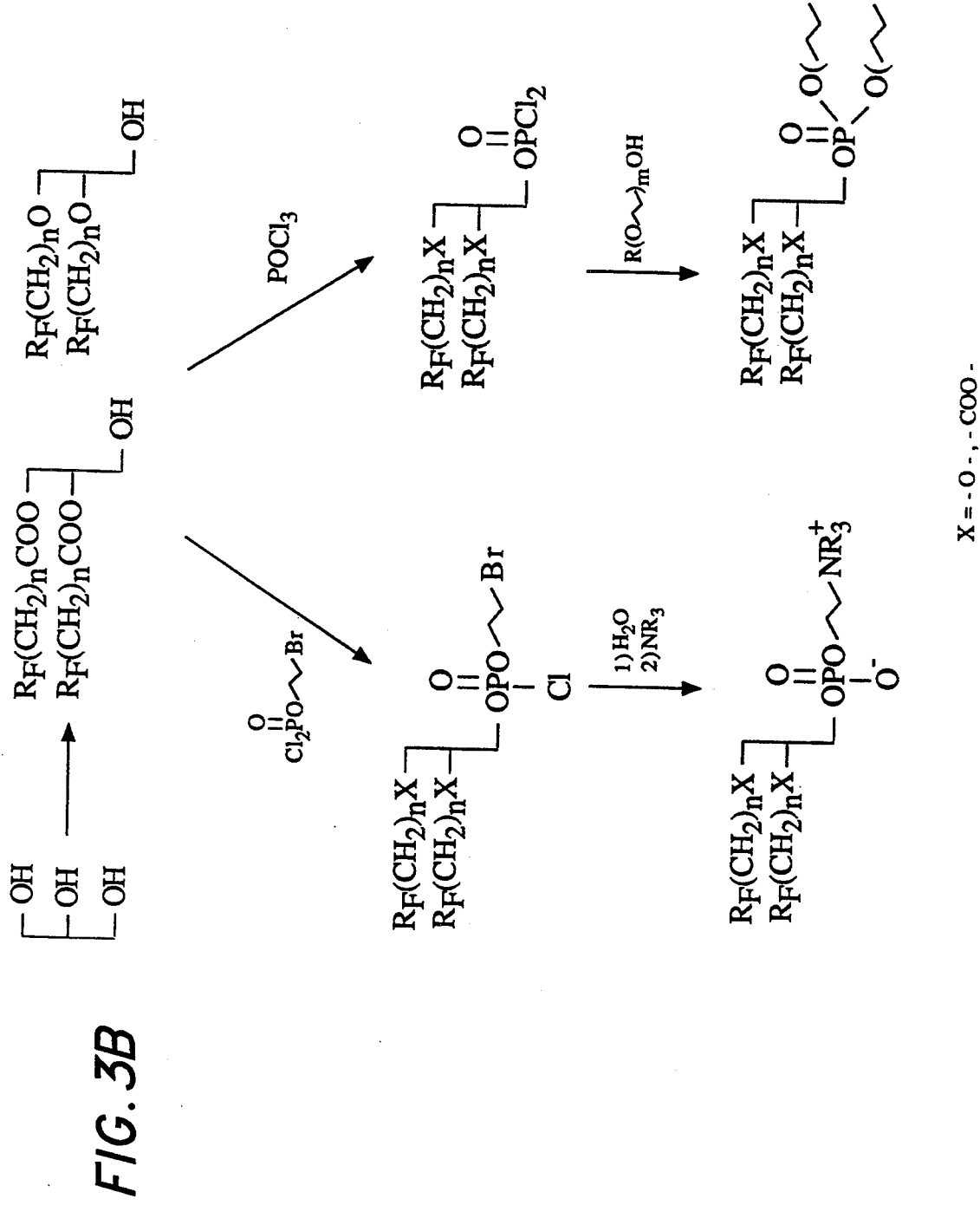
Figure 4:
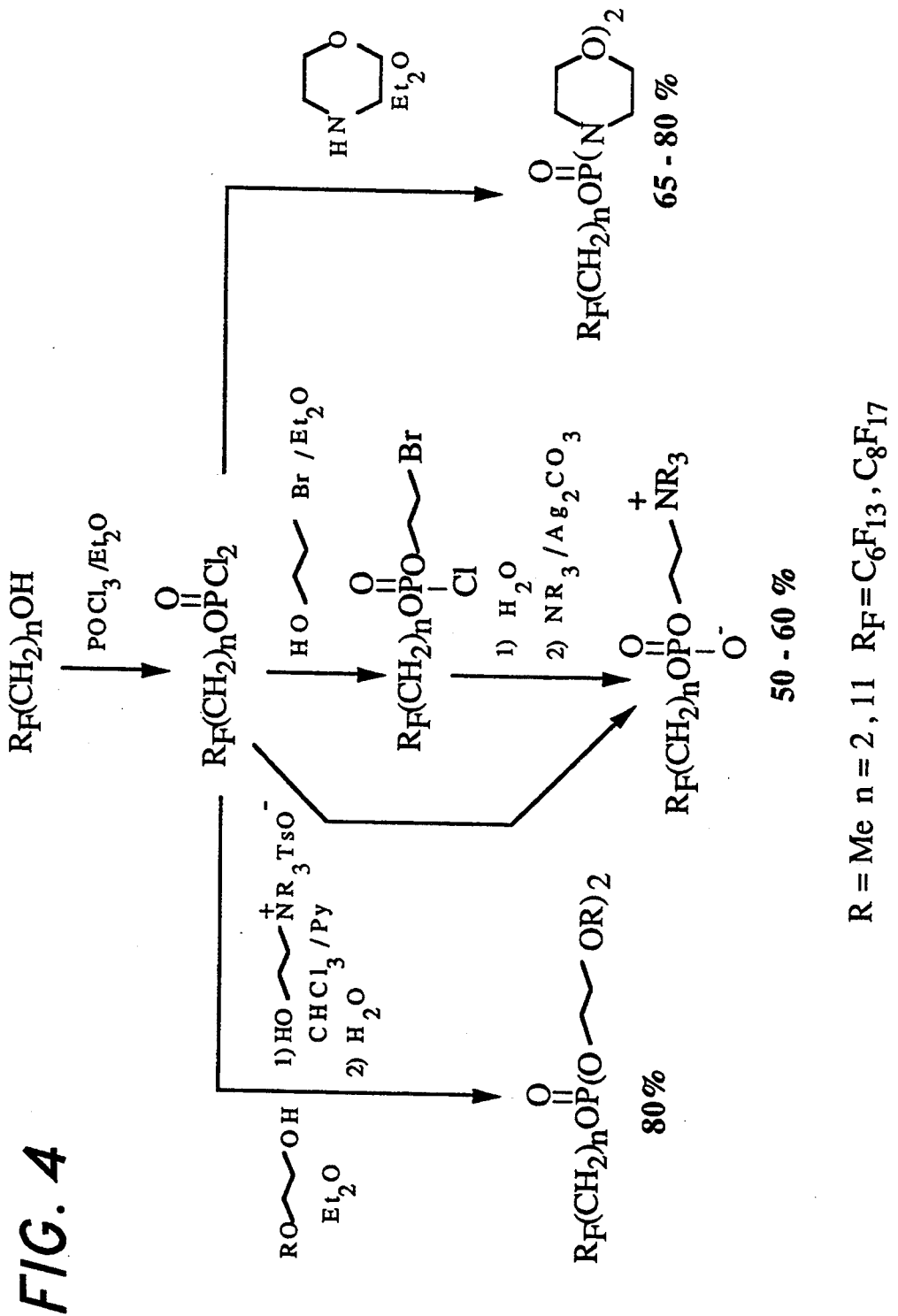
FIG. 4 shows in more detail part of the synthetic scheme shown in FIG. 3.
Figure 5:
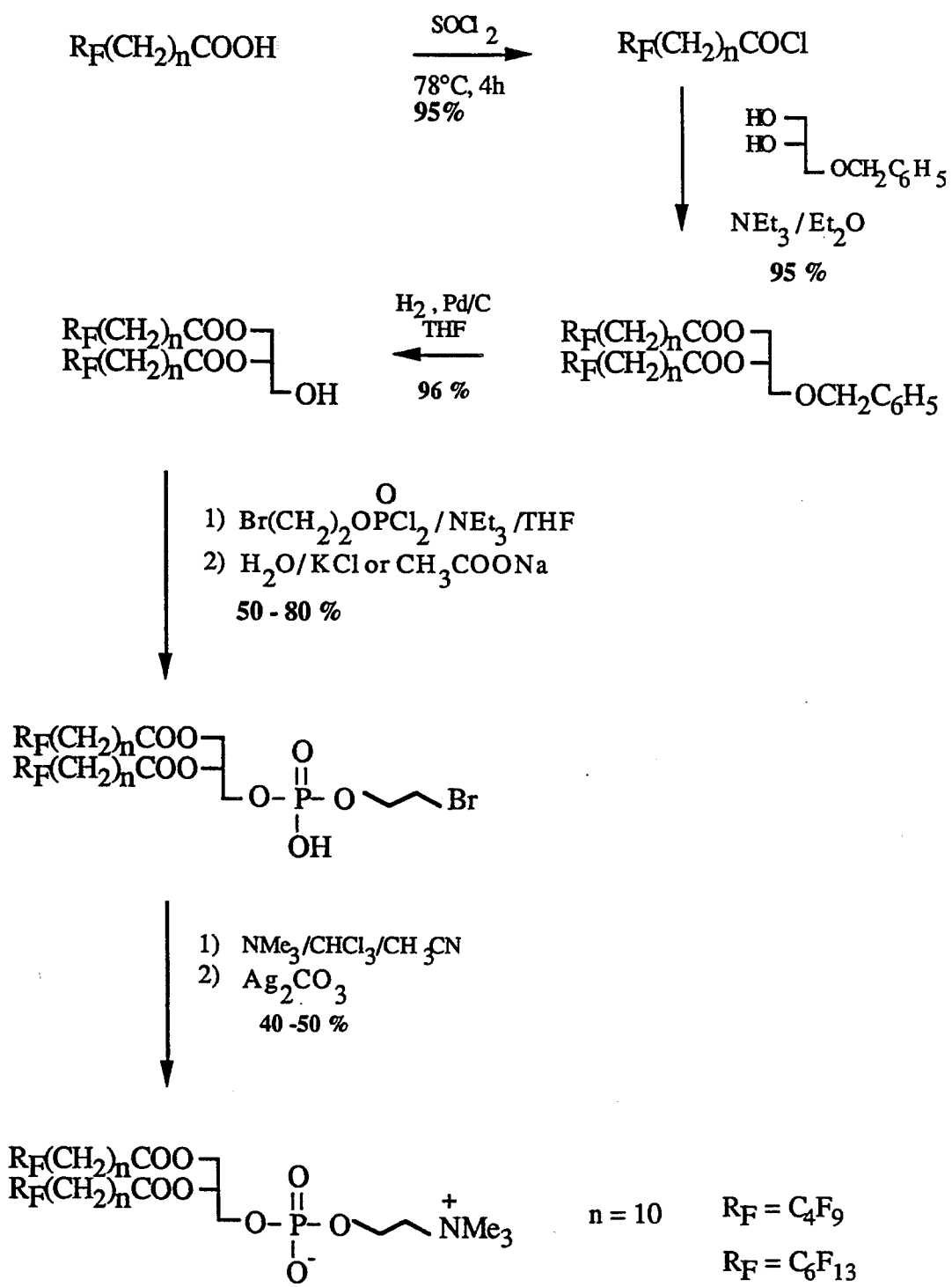
FIG. 5 shows further exemplary synthetic schemes for preparing certain compounds of the invention, which again may be extended by analogy for the preparation of other compounds of the invention.

The above and other synthetic routes are illustrated in FIGS. 3 to 5, the procedures of which may be generalized to make other compounds of the invention.

Compounds of the invention are useful in the preparation of fluorocarbon emulsions, which in turn are useful as oxygen-carrying blood substitutes among other medical and diagnostic applications. Processes by which such emulsions can be prepared will be familiar to those skilled in the art and include the use of mechanical high pressure homogenizers such as a Gaulin homogenizer, a Microfluidizer ™ (Microfluidics, Inc., Boston, Mass.) or even, if appropriate and economically feasible, ultrasonics. Particularly suitable preparative techniques are disclosed in EP-A-0231070 and EP-A-0307087 (both in the name of David M. Long, Jr.); compounds in accordance with the first aspect of this invention should be substituted for the surfactants disclosed in the above European patent applications (or in any other known and suitable formulation) in the same or suitably modified amounts. To the extent that the law allows, EP-A-02.31070 and EP-A-0307087 are both incorporated by reference.

According to a fifth aspect of the invention, there is provided an emulsion comprising an oily phase, an aqueous phase and a surfactant in accordance with the first aspect. Various appropriate additives may also be present, for example those disclosed in EP-A-0231070 and EP-A-0307087.

Compounds of the invention are also useful in the preparation or modification of lipid membranes and liposomes or niosomes, which in turn are useful as drug, or drug carriers, (including in connection with oxygen carriers such as hemoglobin or modified hemoglobin or synthetic chelates), contrast agents, delivering and targeting systems, or in cosmetics. Processes by which such lipid membranes, liposomes or niosomes can be prepared will be familiar to those skilled in the art and include the use of solvent techniques, injection, or the use of ultrasonics or of a mechanical high pressure homogenizer such as a Gaulin homogenizer or a Microfluidizer ™.

The term "emulsion" is intended to include dispersions, liposomes, niosomes, vesicles, gels, micellar solutions, and microemulsions, or similarly structured phases, and containing polar or non-polar substances, including drugs, or an oil, which may be hydrocarbonated or not, and the emulsion may contain one or more other surfactants.

The non-polar substances or oils may be highly fluorinated or perfluorinated. Thus the present invention contemplates a fluorocarbon as the oily phase, in which case such compositions are useful as blood substitutes and contrast enhancement agents. In such compositions, the highly fluorinated or perfluorinated compounds, with molecular weights between about 400 and 700, may be chosen especially, but not exclusively, among at least one of the following: the bis(F-alkyl)-1,2-ethenes and more particularly the bis(F-butyl)-1,2-ethenes, the F-isopropyl-1, F-hexyl-2-ethenes and the bis(F-hexyl)-1,2-ethenes, the perfluorodecalins, the perfluoromethyldecalins, the perfluoro-dimethyldecalins, the perfluoromono- and dimethyladamantanes, the perfluoro-trimethylbicyclo/3,3,1/nonanes and their homologues, ethers of formula (CF$_3$)CFO(CF$_2$CF$_2$)OCF(CF$_3$)$_2$, (CF$_3$)$_2$CFO(CF$_2$CF$_2$)$_3$OCF(CF$_3$)$_2$, (CF$_3$)$_2$CFO(CF$_2$CF$_2$)$_2$F, (CF$_3$)$_2$CFO(CF$_2$CF$_2$)$_3$F, F[CF(CF$_3$)CF$_2$O]$_2$CHFCF$_3$, (C$_6$F$_{13}$)$_2$O, the amines N(C$_3$F$_7$)$_3$, N(C$_4$F$_9$)$_3$, the perfluoromethyl-quinolidines and perfluoroisoquinolidines, the halogen derivatives C$_6$F$_{13}$Br, C$_8$F$_{17}$Br, C$_6$F$_{13}$CBr$_2$CH$_2$Br, 1-bromoheptadecafluoro-4-isopropylcyclohexane and analogues, it being understood that the compounds can be used separately or in the form of mixtures. Such compositions are more particularly used as gas carriers, and in particular for oxygen in living surroundings, for human and veterinary medical applications, in particular as blood substitutes, means to treat cerebral and cardiac ischemia in preoperative hemodilution, for the preservation of organs, tissues, embryos, semen, medium usable in cardiovascular therapy and surgery, for example as a cardioplegic, reperfusion, or coronary angioplasty, solution medium usable as adjuvant for radiotherapy or chemotherapy of cancer, or medium usable as medicinal vehicle, as contrast agents or diagnosis by X-rays, magnetic resonance or ultrasound radiography.

The compositions of the present invention may comprise 5–80% (vol/vol) of the oily phase, e.g., a nonpolar compound, and 0.5–12% (vol/vol) of at least one surfactant of the first aspect, and the remainder being the solvent, e.g. water, and optionally, various additives, including inorganic salts, generally in the form of buffers, which allow adjustment of the pH and obtaining of an isotonic composition.

The surfactant comprises at least one of the fluorinated surfactants of the first aspect of the present invention, optionally in combination with conventional surfactant, the fluorinated surfactants of the invention representing, by volume, from 1% to 100% of the total volume of surfactants. The present invention is illustrated by means of the following Examples, which are not intended to be unduly limiting, since the methods set forth therein are broadly applicable to the preparation of all of the compounds disclosed.

EXAMPLE 1: Synthesis of [2-(F-hexyl)ethyl] dimorpholinohosphoramidate 1

20.89 g of 2-(F-hexyl)-ethanol and 18 ml of triethylamine were allowed to react in dry ether at 0° C. and under argon with 8.8% of phosphorus oxychloride to give [2-(F-hexyl) ethoxy] phosphoryl dichloride A solution of 12.5 g of morpholine and 18 ml of triethylamine in ether was then added dropwise to the cooled reaction mixture. After treatment, the oily clear residue was distilled (Eb=150° C./0.03 mmHg), yielding 26.72 g (80%) of [2-(F-hexyl) ethyl] dimorpholinophosphoramidate 1.

F=25° C.±1° C.; C found (calculated) 33.40 (32.99); H 3.52 (3.44); N 4.93 (4.81); F 40.42 (42.44); P 5.36 (5.83); MS (LID/IC/NH$_3$); m/e (%): M+1 583(100); IR ($v$cm$^{-1}$); 1250-1150 (P=O, C—F), 972 (P—N); NMR $^1$H ($\delta$ppm, CDCl$_3$):2.56 (tt, 2H,$^3$J$_{HH}$=5.3 Hz, $^3$J$_{HF}$=18.5 Hz, R$_F$CH$_2$), 3.17 (dt, 8H, $^3$J$_{HH}$=5.3 Hz, $^3$J$_{PH}$=2.7 Hz, NCH$_2$), 3.68 (t, 8H, $^3$J$_{HH}$=5.3 Hz, CH$_2$OCH$_2$), 4.32 (dt, 2H, $^3$J$_{HH}$=5.3 Hz, $^3$J$_{PH}$=7.9 Hz, CH$_2$OP); NMR $^{13}$C($\delta$ppm, CDCl$_3$): 31.9 (td, $^1$J$_{CF}$=21 Hz, $^3$J$_{CP}$=7 Hz, R$_F$CH$_2$), 44.5 (s, PNCH$_2$), 57.1 (d, $^2$J$_{PC}$=5 Hz, R$_F$CH$_2$CH$_2$), 67.1 (d, $^3$J$_{PC}$=8 Hz, CH$_2$OCH$_2$); NMR $^{31}$P ($\delta$ppm, CDCl$_3$); 14.2; NMR $^{19}$F($\delta$ppm, CDCl$_3$): −81.3 (CF$_3$), −114.0 (CF$_3$CF$_2$), −122.3 (2F), −123.3 (2F), −124.0 (2F), −126.6 (CF$_2$CH$_2$).

EXAMPLE 2: Synthesis of [2-(F-octyl)ethyl] dimorpholinohosphoramidate 2

The experimental procedure described above when applied to 16.5 g of 2-(F-octyl)-ethanol, 5.48 g of phosphorus oxychloride and 7.84 g of morpholine afforded after treatment, chromatography and/or recrystallization from hexane, 17.04 g (70%) of 2 as white crystals.

F=60° C.±1 C; C 31.73 (31.67); H 2.96 (2.93); N 3.90 (4.10); F 47.21 (47.36); P 4.23 (4.54); MS (LID-/IC/NH$_3$); m/e (%), M+1; 683 (100); IR ($v$cm$^{-1}$); 1250-1150 (P=O, C—F), 970 (P—N); NMR $^1$H($\delta$ppm, CDCl$_3$); 2.54 (tt, 2H, $^3$J$_{HH}$=5.3 Hz, $^3$J$_{HF}$=18.5 Hz, R$_F$CH$_2$) ; 3.16 (dt, 8H, $^3$J$_{HH}$=5.3 Hz, $^3$J$_{PH}$=2.7 Hz, NCH$_2$); 3.66 (t, 8H, $^3$J$_{HH}$=5.2 Hz, CH$_2$OCH$_2$); 4.31 (dt, 2H, $^3$J$_{HH}$=5.3 Hz, $^3$J$_{PH}$=7.9 Hz, CH$_2$OP); NMR $^{13}$C ($\delta$ppm, CDCl$_3$); 32.1 (td, $^2$J$_{CF}$=21.5 Hz; $^3$J$_{CP}$=7 Hz, R$_F$CH$_2$), 44.6 (s, NCH$_2$), 57.3 (m, $^2$J$_{PC}$=5 Hz, R$_F$CH$_2$CH$_2$), 67.1 (d, J$_{CP}$=5 Hz, CH$_2$OCH$_2$); NMR $^{31}$P ($\delta$ppm, CDCl$_3$); 14.2 ; NMR $^{19}$F ($\delta$ppm, CDCl$_3$) ; −81.3 (CF$_3$); −114.0 (CF$_3$CF$_2$); −122.4 (6F); −123.2 (2F); −124.0 (2F); −126.6 (CF$_2$CH$_2$)

EXAMPLE 3: Synthesis of [11-(F-hexyl)undecyl] dimorpholinohosphoramidate 3

The previous method when applied to 3.2 g of 11-(F-hexyl) undecanol, 1.02 g of phosphorus oxychloride and 1.73 g of morpholine, gave after chromatography 3.0 g (65%) of the phosphoramidate 3

F=20° C.±1° C.; C 42.56 (42.37); H 5.24 (5.36); N 3.66 (3.95); F 34.03 (34.89); P 4.43 (4.38) ; MS (LID-/IC/NH$_3$): m/e (%): M+1 683 (100); IR ($v$cm$^{-1}$); 2929, 2954 (C—H); 1240-1150 (P=O, C—F); 972 (P—N); NMR $^1$H ($\delta$ppm, CDCl$_3$): 1.33 ("s", 18H, (CH$_2$)$_9$); 1.80 (m, 2H, R$_F$CH$_2$); 3.14 (dt, 8H, $^3$J$_{HH}$=5.3 Hz, $^3$J$_{PH}$=2.7 Hz, NCH$_2$); 3.64 (t, 8H, $^3$J$_{HH}$=5.3 Hz, CH$_2$OCH$_2$); 3.98 (dt, 2H, $^3$J$_{HH}$=5.3 Hz; $^3$J$_{PH}$=7.9 Hz, CH$_2$OP); NMR $^{13}$C ($\delta$ppm, CDCl$_3$): 20.0 (t, $^3$J$_{CF}$=5 Hz, R$_F$CH$_2$CH$_2$), 25.7, 29.1, 29.2, 29.3, 29.5 30.6 (all s, 8CH$_2$), 30.8 (t, $^2$J$_{CF}$=20 Hz, R$_F$CH$_2$); 44.7 (s, NCH$_2$), 65.5 (d, $^2$J$_{CP}$=4.8 Hz, CH$_2$OP), 67.2 (d, $^3$J$_{CP}$=6 Hz, CH$_2$OCH$_2$); NMR $^{31}$P ($\delta$ppm, CDCl$_3$): 13.9; NMR $^{19}$F ($\delta$ppm, CDCl$_3$): −81.3 (CF$_3$) ; −114.9 (CF$_3$CF$_2$), −122.3 (6F); −123.2 (2F); −124.0 (2F); −126.6 (CF$_2$CH$_2$).

EXAMPLE 4: Synthesis of [11-(F-octyl)undecyl] dimorpholinohosphoramidate 4

As in Example 3, the reaction between 3.5 g of 11-(F-octyl) undecanol-1, 0.91 g of phosphorous oxychloride and 1.3 g of morpholine, afforded, after treatment and chromatography 3.40 g (71%) of the phosphoramidate 4.

F=65° C.±1° C.; C 40.08 (40.10); H 4.83 (4.70); N 3.43 (3.46); F 38.50 (39.97); P 3.75 (3.84); IR ($v$cm$^{-1}$); 2924, 2853 (C—H); 1258-1205 (P=O, C—F); 974 (P—N); NMR $^1$H ($\delta$ppm, CDCl$_3$): 1.32 (broad s, 18H, (CH$_2$)$_9$; 2.03 (m, 2H, R$_F$CH$_2$); 3.16 (dt, 8H, $^3$J$_{HH}$=5.3 Hz, $^3$J$_{PH}$=2.7 Hz, NCH$_2$); 3.66 (t, 8H, $^3$J$_{HH}$=5.3 Hz, CH$_2$OCH$_2$); 3.96 (dt, 2H, $^3$J$_{HH}$=5.3 Hz, $^3$J$_{PH}$=7.9 Hz, CH$_2$OP); NMR $^{13}$C ($\delta$ppm, CDCl$_3$): 20.5 (t, $^3$J$_{CF}$=5 Hz, R$_F$CH$_2$CH$_2$), 26.0, 29.3, 30.0, 30.1, 30.2, 31.5 (all s, 8 CH$_2$), 31.7 (t, $^2$J$_{CF}$=20 Hz, R$_F$CH$_2$), 44.8 (s, NCH$_2$), 65.7 (d, $^2$J$_{CP}$=5 Hz, CH$_2$OP), 67.5 (d, $^3$J$_{CP}$=6 Hz, CH$_2$OCH$_2$); NMR $^{31}$P ($\delta$ppm, CDCl$_3$): 13.9; NMR $^{19}$F ($\delta$ppm, CDCl$_3$); −81.3 (CF$_3$); −114.9 (CF$_3$CF$_2$); −122.3 (6F); −123.2 (2F); −124.0 (2F); −126.6 (CF$_2$CH$_2$).

EXAMPLE 5: Synthesis of [2-(F-octyl) ethyl] [2'-N,N,N trimethylamino ethyl ] phosphate 5

2-(F-octyl)-ethanol (21.30 g) and triethylamine (14.5 ml) were allowed to react in dry ether at 0° C. and under argon first with phosphorus oxychloride (7.04 g) then with 5.74 g of bromoethanol and 10 ml triethylamine to give 29.02 g (94%) of [2- (F-octyl) ethoxy] [2'-bromoethyl] phosphoryl chloride.

28.86 g of this compound, dissolved in acetonitrile, were hydrolyzed at 0°–5° C. into 27.65 g (98%) of [2-(F-octyl) ethyl] [2'- bromoethyl] phosphate.

A large excess of trimethylamine was bubbled through a 50/50 chloroform/acetonitrile solution of the latter compound. The mixture, heated at 40° C. for 15 hours, was then allowed to react with silver carbonate (5.91 g), leading after treatment to 18.71 g (71%) of 5.

F:decomposition 267° C.; C(+H$_2$O) 28.12 (27.82); H 3.01 (2.94); N 2.15 (2.16); F 48.29 (49.92); P 4.59 (4.79); MS (LID/IC/NH$_3$) m/e (%); M+1 630 (2.5); IR ($v$cm$^{-1}$); 1250-1200 (P=O, C—F); NMR $^1$H ($\delta$ppm, CD$_3$OD); 2.55 (tt, 2H, $^3J_{HH}$=5.3 Hz, J$^3_{HF}$=18.5 Hz; R$_F$CH$_2$); 3.24 (s, 9H, NCH$_3$); 3.66 (m, 2H, CH$_2$N); 4.28 (m, 4H, CH$_2$O): NMR $^{13}$C ($\delta$ppm, CD$_3$OD); 33.9 (dt, $^2J_{CF}$=20.5 Hz, $^3J_{PC}$=7 Hz, R$_F$CH$_2$); 55.3 (3 lines due to J$_{CN}$=4 Hz, NCH$_3$); 59 (m, $^3J_{PC}$=5 Hz, R$_F$CH$_2$CH$_2$), 61 (d, $^2J_{(d}$, $^2J_{CP}$=5.4 Hz, OCH$_2$CH$_2$N); 68.1 (m, $^1J_{CN}$=4 Hz, $^3J_{PC}$=7 Hz, CH$_2$N); NMR $^{31}$P ($\delta$ppm, CD$_3$OD); 0.50; NMR $^{19}$F ($\delta$ppm, CD$_3$OD); −80.7 (CF$_3$); −113.0 (CF$_3$CF$_2$); −121.3 (6F); −122.2 (2F); −123.1 (2F); −125.7 (CF$_2$CH$_2$).

EXAMPLE 6: Synthesis of [11-(F-octyl)undecyl] [2'-N,N,N trimethylamino ethyl] phosphate 6

The process of Example 5 applied first to 60.70 g of 11-(F-octyl)-undecanol, 36 ml of triethylamine and 15.74 g of phosphorus oxychloride, then to 12.86 g of bromoethanol and 20 ml of triethylamine yielded 78.42 g (96%) of [11-(F-octyl) undecyl] (2'-bromoethyl) phosphoryl chloride. After hydrolysis into [11-(F-octyl)undecyl] (2'-bromoethyl] phosphate and reaction with trimethylamine, then with 17.70 g of silver carbonate and successive recrystallizations from chloroform-methanol, 39.02 g (50% global) of 6 were obtained.

F decomposition>250° C.; C (+H$_2$O) 37.14 (37.26); H 5.20 (4.78); N 2.07 (1.81); F 40.83 (41.78); P 4.20 (4.01); IR ($v$cm$^{-1}$); 2924-2954 (C—H); 1236-1204 (P=O, C—F); NMR $^1$H ($\delta$ppm, CD$_3$OD): 1.34 (broad, s, 18H, (CH$_2$)$_9$); 2.03 (tt, 2H, R$_F$CH$_2$ ); 3.22 (s, 9H), NCH$_3$), 3.64 (m, 2H, CH$_2$Br); 3.85 (dt, 2H, $^3J_{PH}$=6 Hz, (CH$_2$)$_9$CH$_2$OP); 4.26 (m, 2H, $^3J_{PH}$=4 Hz, OCH$_2$CH$_2$; NMR $^{13}$C ($\delta$ppm, CD$_3$OD): 2.12 (J<2Hz, R$_F$CH$_2$CH$_2$), 26.9 30. . .30.8 , [CH$_2$)$_7$], 31.8 (CH$_2$CH$_2$CH$_2$OP) (31.9 (t, $^2J_{CF}$=22 Hz, CF$_2$CH$_2$), 54.6 (three lines due to $^1J_{CN}$=4 Hz, NCH$_2$), 60.15 (d, $^2J_{CP}$=4.9 Hz, (CH$_2$)$_7$CH$_2$O), 66.75 (d, $^2J_{CP}$=6.2 Hz, O CH$_2$CH$_2$N), 67.4 (m, CH$_2$N); NMR $^{19}$F ($\delta$ppm, CD$_3$OD): −80.9 (CF$_3$); −114.0 (CF$_3$CF$_2$); −121.5 (6F); −122.3 (2F); −123.1 (2F); −125.9 (CF$_2$CH$_2$): NMR $^{31}$P ($\delta$ppm, CD$_3$OD): 0.50.

EXAMPLE 7: Synthesis of [5-(F-hexyl)pentyl][2'N,N,N trimethylamino ethyl] phosphate 7

5-(F-hexyl) pentanol (3.1 g) and triethylamine (1.3 ml were allowed to react in dry ether at −0° C. and under argon with phosphorus oxychloride (1.42 g). after evaporation of the solvent and redissolution in dry chloroform, a solution of choline tosylate (3.0 g) in pyridine (5.2 ml) was added. After hydrolysis and treatment, 3.2 g (73%) of 7 were obtained.

C 33.71 (33.64); H 4.09 (4.06); N 2.44 (2.45); F 41.20 (43.23); P 5.50 (5.42); RNM $^1$H (67 ppm, CD$_3$OD, TMS): 1.32-1.80 (m, 6H, R$_F$CH$_2$(CH$_2$)$_3$), 1.98-2.30 (m, 2H, R$_F$CH$_2$—), 3.26 (s, 9H, N(CH$_3$)$_3$), 3.70 (m, 2H, —CH$_2$N),3.90 (dt, $^3J_{HH}$=6.6 Hz, $^3J_{HP}$=5.5 Hz, 2H, R$_F$(CH$_2$)$_4$CH$_2$OP), 4.28 (m, 2H, OCH$_2$CH$_2$N): RMN $^{13}$C($\delta$ppm, CD$_3$OD, TMS); 21.0 (t, $^3J_{CF}$=4.7 Hz, CF$_2$CH$_2$CH$_2$) 2.65 (s, R$_F$(CH$_2$)$_2$CH$_2$), 31.4 (d, $^3J_{CP}$=7.2 Hz, R$_F$(CH$_2$)$_3$CH$_2$CH$_2$OP); 3.16 (t, $^2J_{CF}$=22.3 Hz, R$_F$CH$_2$), 54.6 (t, $^1J_{CN}$=3.7 Hz, N(CH$_3$)$_3$), 60.2 (d, $^2J_{CP}$=4.9 Hz, OCH$_2$CH$_2$N), 66.4 (d, $^2J_{CP}$=6.1 Hz, R$_F$(CH$_2$) $_4$CH$_2$OP), 67.4 (m, OCH$_2$CH$_2$N); RMN $^{19}$F ($\delta$ppm, CD$_3$OD, CFCl$_3$): −81.3 (3F, CF$_3$), −114.1 (2F, CF$_2$CH$_2$), −121.7 à −123.2 (6F), CF$_3$CF$_2$(CF$_2$)$_3$), −126.2 (2F, CF$_3$CF$_2$); RMN $^{31}$P ($\delta$ppm, CD$_3$OD, H$_3$PO$_4$): 0.74 (s).

EXAMPLE 8: Synthesis of [5-(F-octyl)pentyl][2'-N,N,N trimethylamino ethyl] phosphate 8

The process of Example 7 applied first to 10.1 g of 5-(F-octyl) pentanol, 3.5 ml of triethylamine and 3.85 g of phosphorus oxychloride, then to 8.25 g of choline tosylate and 12 ml of pyridine yielded after hydrolysis and treatment 9.4 g (70%) of 8. C 32.20 (32.20); H 3.78 (3.45); N 2.06 (2.09); F 44.82 (48.40); P 4.80 (4.61); RMN $^1$H (67 ppm, CD$_3$OD, TMS): 1.45-1.80 (m, 6H, R$_F$CH$_2$(CH$_2$)$_3$); 2.05-2.37 (m, 2H, R$_F$CH$_2$—); 3.27 (s, 9H, N(CH$_3$)$_3$); 3.68 (m, 2H, —CH$_2$N);3.94 (dt, $^3J_{HH}$=6.0 Hz, $^3J_{HP}$=6.3 Hz, 2H, R$_F$(CH$_2$)$_4$CH$_2$OP); 4.28 (m, 2H, OCH$_2$CH$_2$N); RMN $^{13}$C ($\delta$ppm, CD$_3$OD, TMS); 20.1 (t, $^3J_{CF}$=3.8 Hz, CF$_2$CH$_2$CH$_2$); 26.4 (s, R$_F$(CH$_2$)$_2$CH$_2$); 3.14 (d, $^3J_{CP}$=7.4 Hz, R$_F$(CH$_2$)$_3$CH$_2$CH$_2$OP); 31.6 (t, $^2J_{CF}$=22.1 Hz, R$_F$CH$_2$); 54.6 (t, $^1J_{CN}$=4.0 Hz, N(CH$_3$)$_3$); 60.2 (d, $^2J_{CP}$=4.8 Hz, OCH$_2$CH$_2$N); 66.4 (d, $^2J_{CP}$=6.2 Hz, R$_F$(CH$_2$)$_4$CH$_2$OP); 67.5 (m, OCH$_2$CH$_2$N) ; RMN $^{19}$F ($\delta$ppm, CD$_3$OD, CFCl$_3$); −81.0 (3F, CF$_3$); −113.9 (2F, CF$_2$CH$_2$); −121.4 to −123.0 (10F, CF$_3$CF$_2$(CF$_2$)$_3$); −125.9 (2F, CF$_3$CF$_2$); RMN $^{31}$P ($\delta$ppm, CD$_3$OD, H$_3$PO$_4$): 1.18 (s).

EXAMPLE 9: Synthesis of [5-(F-octyl)pentyl][2'N ethyl-N,N dimethylamino ethyl] phosphate 9

The process of Example 7 applied first to 5.2 g of 5-(F-octyl) pentanol, 1.8 ml of triethylamine and 1.96 g of phosphorus oxychloride, then to 4.45 g of N-ethyl-N,N-dimethyl-ethanolamine tosylate and 6.2 ml of pyridine yielded after hydrolysis and treatment 4.7 g (67%) of 9.

RMN $^1$H ($\delta$ppm, CD$_3$OD, TMS): 1.40 (t, $^3J_{HH}$=7.2 Hz, 3H, NCH$_2$CH$_3$); 1.45-1.80 (m, 6H, R$_F$CH$_2$(CH$_2$)$_3$); 2.05-2.33 (m, 2H, R$_F$CH$_2$—); 3.16 (s, 6H, N(CH$_3$)$_2$); 3.52 (q, $^3J_{HH}$=7.2 Hz, 2H, NCH$_2$CH$_3$); 3.60 (m, 2H, —CH$_2$N); 3.90 (dt, $^3J_{HH}$=6.1 Hz, $^3J_{NP}$=6.3 Hz, 2H, R$_F$(CH$_2$)$_4$CH$_2$OP); 4.22 (s large, 2H, OCH$_2$CH$_2$N); RMN $^{13}$C ($\delta$ppm, CD$_3$OD, TMS): 8.5 (s, NCH$_2$CH$_3$); 21.1 (t, $^3J_{CF}$=4.6 Hz, CF$_2$CH$_2$CH$_2$); 26.5 (s, R$_F$(CH$_2$)$_2$CH$_2$); · 31.5 (d, $^3J_{CP}$=7.4 Hz, R$_F$(CH$_2$)$_3$CH$_2$CH$_2$OP); 31.7 (t, $^2J_{CF}$=22.2 Hz, R$_F$CH$_2$); 51.6 (s, large, N(CH$_3$)$_2$); 60.1 (d, $^2J_{CP}$=5.1 Hz, OCH$_2$CH$_2$N); 62.3 (s large, NCH$_2$CH$_3$); 64.6 (m, OCH$_2$CH$_2$N); 66.5 (d, $^2J_{CP}$=5.6 Hz, R$_F$(CH$_2$)$_4$CH$_2$OP); RMN $^{19}$F ($\delta$ppm, CD$_3$OD), CFCl$_3$); −81.0 (3F, CF$_3$); −113.9 (2F, CF$_2$CH$_2$); −120.3 to −123.0 (10F, CF$_3$CF$_2$(CF$_2$)$_3$); −125.9 (2F, CF$_3$CF$_2$); RMN $^{31}$P (δppm, CD$_3$OD, H$_3$PO$_4$): 1.04 (s).

EXAMPLE 10: Synthesis of [1,2-di[(11-F-hexyl) undecaoyl] 3-[2'-(N,N,N-trimethylamino) ethyl phosphoryl] rac-glycerol 10

1) Synthesis of 1,2-Di[(11-F-hexyl) undecaoyl] 3-benzyl rac-glycerol 1-benzyl rac-glycerol (3.92 g) and triethylamine were allowed to react in Et$_2$O at 0° C. under argon with 11-F-hexyl-undecanoyl chloride (24.56 g). After chromatography and recristallization, 23.89 g (95%) of 1,2-di[(11-F-hexyl) undecanoyl] 3-benzyl rac-glycerol as a white solid were obtained.

C 46.00 (45.76), H 4.39 (4.51), F 42.97 (42.77); IR (υcm$^{-1}$, KBr); 1742 (C=O), 1240–1100 (CF), 735, 702 (monosubstituted benzene); NMR $^1$H (δppm, CDCl$_3$, TMS): 1.20–2.60 (m, 40H, (CH$_2$)$_{10}$), 3.6 (d, $^3J_{HH}$=5.3 Hz, 2H, CH$_2$OBz), 4.13–4.55 (m, 2H, COOCH$_2$CH), 4.66 (s, 2H, CH$_2$Ph), 5.20–5.50 (m, 1H, CH), 7.46 (s, 5H, Ph); NMR $^{13}$C (δppm, CDCl$_3$/CD$_3$OD, TMS) ; 20.21 (t, $^3J_{CF}$=3.7 Hz, CF$_2$CH$_2$CH$_2$), 24.96 and 25.03 (s, CH$_2$CH$_2$CO), 29.19, 29.30 and 29.43 (s, (CH$_2$)$_6$), 31.03 (t, $^2J_{CF}$=22.3 Hz, CF$_2$CH$_2$), 34.20 and 34.41 (s, CH$_2$CO), 62.79 and 68.46 (s, CH$_2$CHCH$_2$), 70.21 (s, CH), 73.45 (s, CH$_2$Ph), 127.71 and 128.51 (s, C ortho and meta), 127.86 (s, C para), 137.89 (s, CH$_2$—C(Ph), 173.13 and 173.41 (s, CO).

2) Synthesis of 1,2-di[(11-F-hexyl) undecaoyl] 3-benzyl rac-glycerol 1.44 g of 10% palladium on activated charcoal were added under argon to a solution of 1,2-di[(11-F-hexyl) undecaoyl] 3-benzyl rac-glycerol (20.62 g) in THF. The stirred suspension was kept under hydrogen pressure (1.6 bar) until hydrogenolysis was complete. The catalyst was filtered off and the filtrate was either concentrated or used directly in the next step. The product was stored at 4° C.

IR (υcm$^{-1}$, KBr): 3500 (OH), 1742 (C=O), 1232–1100 (CF); NMR $^1$H (δppm, CDCl$_3$, TMS): 1.16–2.60 (m, 40H, (CH$_2$)$_{10}$), 3.76 (d, $^3J_{HH}$=6 Hz,, 2H, CH$_2$OH); 4.16–4.63 (m, 2H, OCH$_2$), 5.13 (m, 1H, CH).

3) Synthesis of 1,2-di[(11-F-hexyl) undecaoyl] 3-[2'-(N,N,N-trimethylamino) ethyl] phosphoryl rac-glycerol, 10

A solution of 1,2-di[(11-F-hexyl) undecaoyl] rac-glycerol (2.59 g) in THF was added to a cooled solution of (2-bromoethyl) dichlorophosphate (0.82 g) and triethylamine (1.23 g) in THF. The mixture was first stirred at room temperature, then refluxed gently. After cooling at 0° C., 4.5 ml of water were added and stirring was continued. The mixture was decanted and the aqueous phase extracted with CHCl$_3$. After evaporation, the crude residue (3.33 g) was dissolved in CHCl$_3$ and CH$_3$CN to which 1.23 g of trimethylamine was added. The mixture was heated for 24 h at 50° C. After cooling, Ag$_2$CO$_3$ (0.56 g) was added and stirring was continued for 3 hours. Purification over silica gel and recristallization afforded 1.08 g (32%) of 10.

NMR $^1$H (δppm, CDCl$_3$, TMS): 1.30 (bs, 24 H, (CH$_2$)$_6$), 1.60 (m, 8H, CH$_2$ in β from CF$_2$ and CO); 1.90–2.27 (m, 4H, CF$_2$CH$_2$ ); 2.25–2.40 (m, 4H, CH$_2$CO), 3.33 (s, 9H, NCH$_3$), 3.63 (m, 2H, CH$_2$N); 4.00 (dd, 2H, $^3J_{HH}$=6.2 Hz, $^3J_{HP}$=6.7 Hz, CHCH$_2$OP ); 4.18 and 4.45 (part AB of an ABX system, $^2J_{AB}$=12.3 Hz, $^3J_{AX}$=7 Hz, $^3J_{BX}$=3.3 Hz, 2H, CH$_2$CHCH$_2$OP); 4.27 (m, 2H, OCH$_2$CH$_2$N), 5.25 (m, 1H, CH); NMR $^{13}$C (δppm, CDCl$_3$/CD$_3$OD,TMS): 20.56 (t, $^3J_{CF}$=3.6 Hz, CF$_2$CH$_2$CH$_2$), 25.30 and 25.36 (s, CH$_2$CH$_2$CO), 29.53, 29.69 and 29.81 (s, CH$_2$)$_6$), 31.29 (t, $^2J_{CF}$=22.2 Hz, CF$_2$CH$_2$), 34.50 and 34.65 (s, CH$_2$CO), 54.45 (three lines due to $^1J_{CN}$=1.7 Hz, NCH$_3$), 59.57 (d, $^2J_{CP}$=4.9 Hz, POCH$_2$CH$_2$), 63.16 (s, OCH$_2$CH), 64.11 (d, $^2J_{CP}$=5.2 Hz, CHCH$_2$OP), 6.95 (m, CH$_2$N), 70.96 (d, $^3J_{CP}$=8.2 Hz, CH), 174.02 and 174.39 (s, CO); NMR $^{31}$P (δppm, CDCl$_3$/CD$_3$OD, H$_3$PO$_4$) ; −0.68; NMR $^{19}$F (δppm, CDCl$_3$/CD$_3$OD, CFCl$_3$); −81.53 (CF$_3$), −115.12 (CF$_3$CF$_2$), −122.65, −123.66 and −124.16 ((CF$_2$)$_3$), −126.83 (CF$_2$CH$_2$).

EXAMPLE 11: Synthesis of 1,2-di [(11-F-butyl) undecaoyl] 3-[2'-(N,N,N-trimethylamino) ethyl phosphoryl] rac-glycerol 11

The procedure described in Example 10 when applied to 1-benzyl rac-glycerol (5.3 g), (11-F-butyl) undecaoyl chloride (50.3 g) and triethylamine (19 ml) afforded 22.1 g (80%) of 1,2-di [(11-F-butyl) undecaoyl] 3-benzyl rac-glycerol. Hydrogenolysis, then reaction with (2-bromoethyl) dichlorophosphate (6.03 g) and triethylamine (11.04g), followed by hydrolysis, and finally, reaction with trimethylamine (19 g) led to 6.60 g (30%) of 11.

C 44.36 (44.32), H 5.75 (5.64), F 32.66 (33.21), N 1.35 (1.36) P 3.14 (3.01): RMN $^1$H (δppm, CDCl$_3$/CD$_3$OD, TMS): 1.30 (bs, 24 H (CH$_2$)$_6$), 1.60 (m, 8H, CH$_2$ in β from CF$_2$ and CO), 1.93–2.27 (m, 4H, CF$_2$CH$_2$), 2.30 and 2.45 (two t, 4H, CH$_2$CO), 3.25 (s, 9H, NCH$_3$), 3.6–3.7 (m, 2H, CH$_2$N), 4.0 (dd, 2H, $^3J_{HH}$=6.2 Hz, $^3J_{HP}$=6.7 Hz, CH$_2$CH$_2$OP), 4.18 and 4.45 (part AB of an ABX system, $^2J_{AB}$=12.3 Hz, $^3J_{AX}$=7 Hz, $^3J_{BX}$=3.3 Hz, 2H, CH$_2$CHCH$_2$OP), 4.3–4.33 (m, 2H, OCH$_2$CH$_2$N), 5.20 (m, 1H, CH); NMR $^{13}$C (δppm, CDCl$_3$/CD$_3$OD, TMS): 20.44 (t, $^3J_{CF}$=3.6 Hz, CF$_2$CH$_2$CH$_2$), 25.2 (s, CH$_2$CH$_2$CO), 29.42, 29.57 and 29.70 ((CH$_2$)$_6$), 31.08 (t, $^2J_{CF}$=22.3 Hz, CF$_2$CH$_2$), 34.35 and 34.51 (s, CH$_2$CO), 54.27 (three lines due to $^1J_{CN}$=1.7 Hz, NCH$_3$), 59.53 (d, $^2J_{CP}$=4.8 Hz, POCH$_2$), 63.03 (s, OCH$_2$CH), 64.02 (d, $^2J_{CP}$=5 Hz, CHCH$_2$OP), 66.82 (m, CH$_2$N), 70.91 (d, $^3J_{CP}$=8.1 Hz, CH), 173.89 and 174.24 (s, CO); NMR $^{31}$P (δppm, CDCl$_3$/CD$_3$OD, H$_3$PO$_4$): −0.13 (s).

EXAMPLE 12: Synthesis of 1,2-di [(11-F-hexyl) pentanoyl] 3-[2'-(N,N,N-trimethylamino) ethyl phosphoryl] rac-glycerol 12

The procedure described in Example 10 when applied to 1-benzyl rac-glycerol (8.3 g), (11-F-hexyl) pentanoyl chloride (42 g) and triethylamine (13.5 ml) afforded 38.5 g of 1,2-di [(11-F-hexyl) pentanoyl] 3-benzyl rac-glycerol. Hydrogenolysis, then reaction with (2-bromoethyl) dichlorophosphate (10.73 g) and triethylamine (19.73 g), followed by hydrolysis, and finally, reaction with trimethylamine (31.6 g) led to 10.5 g (25%) of 12.

RMN $^1$H (δppm, CDCl$_3$CD$_3$OD, TMS): 1.73 (m, 8H, CH$_2$ in β from CF$_2$ and CO), 2.01–2.29 (m, 4H, CF$_2$CH$_2$), 2.31 and 2.63 (two t, 4H, CH$_2$CO), 3.30 (s, 9H, NCH$_3$), 3.6–3.7 (m, 2H, CH$_2$N), 4.0 (dd, 2H, $^3J_{HH}$=6.2 Hz, $^3J_{HP}$=6.7 Hz, CH$_2$CH$_2$OP), 4.19 and 4.63 (part AB of an ABX system, $^2J_{HH}$=12.3 Hz, $^3J_{AX}$=7 Hz, $^3J_{BX}$=3.3 Hz, 2H, CH$_2$CHCH$_2$OP), 4.3–4.33 (m, 2H, OCH$_2$CH$_2$N), 5.03 (m, 1H, CH); NMR $^{13}$C (δppm, CDCl$_3$/CD$_3$OD, TMS): 19.51 (t, $^3J_{CF}$=3.6

Hz, CF$_2$CH$_2$C̱H$_2$(, 23.98 and 24.00 (s, C̱H$_2$CH$_2$CO), 30.78 (t, $^2J_{CF}$=22.4 Hz, CF$_2$C̱H$_2$), 33.32 and 33.49 (s, CH$_2$CO), 54.05 (three lines due to $^1J_{CN}$=3.7 Hz, NCH$_3$), 58.78 (d, $^2J_{CP}$=4.8 Hz, POC̱H$_2$), 62.73 (s, OC̱H$_2$CH), 63038 (d, $^2J_{CP}$=5 Hz, CHC̱H$_2$OP), 66.41 (m, CH$_2$N), 70.43 (d, $^3J_{CP}$=8.1 Hz, C̱H), 172.56 and 174.89 (s, CO); NMR $^{31}$P (δppm, CDCl$_3$/CD$_3$OD, H$_3$PO$_4$): 0.57 (s), $^{19}$F (δppm, CDCl$_3$,CD$_3$OD, CFCl$_3$; −81.5 (CF$_3$), −115.2 (CF$_3$—CF$_2$); −122.6, −123.6, −124.2 (CF$_2$)$_3$, −128.63 (CF$_3$—CF$_2$).

EXAMPLE 13: Synthesis of 1,2-di [(11-F-butyl) undecyl] 3-[2'-(N,N,N-trimethylamino) ethyl phosphoryl] rac-glycerol 13

1) Synthesis of 1,2-di [(11-F-butyl) undecyl] benzyl-3 rac-glycerol.

6 g of (11-F-butyl) undecyl tosylate in ether were allowed to react with 1 g of benzyl-1 rac-glycerol under phase transfer conditions (KOH, 1N/6 g of (nBu)$_4$N$^+$ HSO$_4^-$). 3.2 g (63%) of the title compound were obtained after 10 days of reaction and chromatography of the organic phase.

NMR $^1$H (δppm, CCl$_4$): 1.02–2.41 (m, 40H, (CH$_2$)$_{10}$); 3.40 (m, 9H, OCH$_2$ and CH) ; 4.47 (s, 2H, C̱H$_2$Ph); 7.26 (s, 5H, Ph).

2) Synthesis of 1,2-di [(11-F-butyl) undecyl] 3-[2'-(N,N,N-trimethylamino) ethyl phosphoryl] rac-glycerol 13.

The process described in Example 10, when applied to 6.7 g of 1,2-di [(11-F-butyl), undecyl] benzyl-3 rac-glycerol led, after hydrogenolysis, reaction with 1.9 g of (2'-bromoethyl) dichlorophosphate and 2 ml of triethylamine, then hydrolysis and finally reaction with trimethylamine (7 g), to 4 g (56%) of 13.

NMR $^1$H (δppm, CDCl$_3$/CD$_3$OD): 1.05–1.65 (m, 36H, (CH$_2$)$_9$); 1.80–2.1 (m, 4H, CF$_2$ CH$_2$); 3.17 (s, 9H, NCH$_3$); 3.35 (t, 2H, $^3J_{HH}$=6.5 Hz, CH$_2$N); 3.40–3.63 (m, 8H, OCH$_2$); 3.79 (t, 2H, $^3J_{HH}$=6.5 Hz); 4.10–4.30 (m, 1H, CH); NMR $^{13}$C (δppm, CDCl$_3$/CD$_3$OD): 20.3 (t, $^3J_{FC}$=3.5 Hz, CF$_2$CH$_2$CH$_2$); 26.3 to 30.3 (nine singlets for the two (CH$_2$)$_8$ chains); 31.0 (t, $^2J_{FC}$=22 Hz, CF$_2$CH$_2$); 54.5 (s, NCH$_3$); 59.4 (d, $^2J_{PC}$=5 Hz, CH$_2$OP); 65.34 (d, $^2J_{PC}$=5 Hz, POCH$_2$CH); 66.65 (d, $^3J_{PC}$=6.5 Hz, CH$_2$N); 70.83, 72.01 (s, CH$_2$CH$_2$O); 70.9 (s, CH$_2$OCH$_2$CH) ; 78.3 (d, $^3J_{PC}$=8 Hz, CH); NMR $^{31}$P (δppm, CDCl$_3$/CD$_3$OD): −0.07 ; NMR $^{19}$F (δppm, CDCl$_3$/CD$_3$OD); −81 (CF$_3$), −114.0 (CF$_3$CF$_2$); −124.4 (CF$_2$); −126.0 (CF$_2$CH$_2$).

EXAMPLE 14: Synthesis of [1',2'-di [(11-F-hexyl) undecanoyl] rac-glyceryl] [di (2'-methoxy-ethyl)] phosphate, 14

1,2-di [(11-F-hexyl) undecanoyl] 3-benzyl rac-glycerol (1.99 g) in ether was added dropwise at 0° C. to a solution of phosphorus oxychloride (0.31 g) and triethylamine (0.66 g) in ether. After stirring at room temperature, 2-methoxyethanol (0.35 g) in ether was added and the mixture was refluxed. Triethylammonium chloride was filtered off, the solvent removed and 15 ml of a mixture of acetonitrile and acetone was added. The soluble fraction was concentrated and purified over silica gel yielding 1 g (42%) of 14.

IR (υcm$^{-1}$, KBr), 1744 (C=O), 1240–1100 (CF). NMR $^1$H (δppm, CDCl$_3$, TMS): 1.10–1.86 (broad s, 32H, (CH$_2$)$_8$); 1.87–2.06 (m, 4H, CF$_2$CH$_2$); 2.20–2.53 (m, 4H, CH$_2$CO); 3.46 (s, 6H, OCH$_3$); 3.66 (m, 4H, CH$_2$OMe); 4.10–4.66 (m, 8H, OCH$_2$); 5.16–5.50 (m, 1H, CH).

EXAMPLE 15: Synthesis of [2-(F-octyl) ethyl][di-(2'-methoxyethyl) phosphate 15

The procedure described for the preparation of 14, when applied to 30.8 g of 2-F-octylethanol, 18 ml of pyridine, 10.2 g of phosphorus oxychloride and to 11.2 g of 2-methoxyethanol led to 26.5 (60%) of 15.

C 29.10 (29.22); H: 2.75 (2.54); F: 48.92 (47.02); P: 4.69 (4.89).

IR (υcm$^{-1}$): 1242 (P=O); 1207–1140 (CF); 979 (P—O). NMR $^1$H (δppm, CDCl$_3$, TMS): 2.61 (m, 2H, CF$_2$CH$_2$); 3.43 (s, 6H, OCH$_3$); 3.66 (m, 4H, CH$_3$OCH$_2$); 4.32 (m, 6H, CH$_2$OP).

EXAMPLE 16: Synthesis of [5-F-hexyl) pentyl][diglycerol] phosphate 16

5-(F-hexyl) pentanol (5.0 g) and triethylamine (2.2 ml) were allowed to react in dry ether at 0° C. and under argon first with phosphorus oxychloride, (2.4 g) then with 10 g of isopropyliden glycerol and 8.2 ml triethylamine to give 5.3 g (60%) of [5-(F-hexyl) pentyl][diisopropyliden glycerol] phosphate.

After hydrolysis in CF$_3$CO$_2$H/H$_2$O 9/1 and treatment, 4.0 g (85%) of 16 were obtained.

SURFACE ACTIVITY

The strong surface activity of the compounds encompassed by this invention is illustrated in particular by the strong lowering of the surface tension ($\gamma_s$) they cause when added to water, as shown by the examples of surface tensions (measured at 20° C. and expressed in milliNewton.meter$^{-1}$) and calculated spreading coefficients collected in the Table below:

| Compound | Concentration in water mmol/l | g/l | $\gamma_s$ (mNm$^{-1}$) (+0.3) | $\gamma_i$ (mNm$^{-1}$) (+0.3) | Spreading Coef. (mNm$^{-1}$) |
|---|---|---|---|---|---|
| 5 | 1.59 | 1 | 23.0 | 4.5 | −4.6 |
| 6 | 1.32 | 1 | 30.0 | 9.4 | −16.5 |
| 2 | 1.47 | 1 | 22.5 | 1.0 | −0.6 |
| 1 | 1.72 | 1 | 22.5 | 2.0 | −1.6 |
| 4 | 0.124 | 0.1 | 22.5 | 1.4 | −1.0 |
| 3 | 0.141 | 0.1 | 24.4 | 7.5 | −0.9 |

More specifically, the action of these compounds at the interface between water and fluorocarbons is demonstrated by the very sharp diminution of the interfacial tension ($\gamma_i$) between water and perfluorodecalin (56 mNm$^{-1}$ in the absence of surfactant) and the increase of the spreading coefficient (−56 mNm$^{-1}$ in the absence of surfactant) as illustrated by examples collected in the same Table.

BIOCOMPATIBILITY

The biocompatibility of compounds belonging to the present invention is illustrated, in particular, by the fact that aqueous solutions or dispersions in 9% of NaCl of these compounds do not perturb the growth and multiplication of lymphoblastoid cell cultures of the Namalva strain with respect to a control of a NaCl 9% solution (100% of growth and viability). Examples are given in the following Table:

| Compound | Concentration | | Cell Culture | |
|---|---|---|---|---|
| | mmol/l | g/l | Growth % | Viability % |
| 5 | 15.9 | 10 | 96 | 102 |
| 2 | 1.47 | 1 | 67 | 106 |
| 10 | 0.81 | 1 | 99 | 95 |
| 11 | 0.97 | 1 | 60 | 83 |
| 13 | 0.99 | 1 | 55 | 91 |

Likewise, the biocompatibility of compounds belonging to the invention is illustrated by the fact that aqueous solutions or dispersions in 9‰ of NaCl of these compounds at the concentrations given in the following table do not cause the hemolysis of human red blood cells.

| Compound | Concentration | |
|---|---|---|
| | mmol/l | g/l |
| 8 | 0.94 | 1 |
| 1 | 17.2 | 10 |
| 5 | 15.9 | 10 |
| 10 | 24.4 | 30 |
| 11 | 97.2 | 100 |
| 12 | 56.2 | 100 |
| 13 | 59.9 | 60 |
| 14 | 14.60 | 10 |

In the same way, the biocompatibility of such compounds is illustrated by the fact that the injection of 500 µl of a solution or a dispersion in NaCl 9‰ of hereafter compounds in concentration given below, into the tail vein of 10 mice of 20–25g caused no deaths, and did not perturb the normal growth of the animals, which was observed for 35 days.

| Compound | concentration g/l |
|---|---|
| 5 | 1 |
| 6 | 1 |
| 10 | 30 |
| 11 | 100 |
| 12 | 100 |
| 13 | 60 |
| 14 | 10 |

PREPARATION OF LIPOSOMES

1) Lipid 12 dissolved in chloroform was placed in a round bottom flask and the solvent evaporated by rotation under argon to produce a uniform film of dry lipid. Residual traces of chloroform were removed under vacuum ($10^{-3}$ mm Hg, 3 h). Dried lipid is suspended in HEPES buffer ($10^{-2}$M, pH 7), vortexed for 5 ran., then probe sonicated (dial 7 on a Branson B30 sonifier, Power 4, Pulse 50, 3 mn.) 15° C. above phase transition temperature, to produce a clear bluish dispersion. Final concentration of 12 is 3% (w/v). Average size measurements were realised by light scattering on a Coulter Model N4SD, sub-Micron Particle Analyser: 0,12 µm.

2) Same dispersion procedure applied to powder lipid 12 produced a clear dispersion with an average particle size 0,12 µm.

Liposomes were observed by electronic microscopy after freeze-etching as unilamellar and multilamellar vesicles. The appearance of liposomes showed no differences or structural distortions after sterilization (8 mn.-121° C.-15 lb/sq.in.). Sterilized dispersions stored at 25° C. showed enhanced stability as time for appearance of a precipitate monitored by visual inspection was higher than 5 months, while hydrocarbonated phosphatidylcholine dispersion's stability is known to be lower than one month.

PREPARATION OF EMULSIONS

TABLE I

| Compound Number | EYP[b] % | F-decalin % | Average Particle Size (µm) | | Relative Increase % |
|---|---|---|---|---|---|
| | | (w/v) | After Preparation[a] | After 1 month at 50° C. | |
| 5 | 1 | 0 | 0.48 | 0.55 | 14 |
| Ref. | 0 | 1 | no emulsion can be prepared | | |
| 5 | 3 | 0 | 50  0.20 | 0.30 | 50 |
| 6 | 3 | 0 | 0.25 | 0.36 | 44 |
| Ref. | 0 | 3 | 0.32 | 0.55 | 72 |

TABLE II

| Compound Number | EYP % (w/v) | F-decalin % (w/v) | Average Particle size (µm) | | | | Relative increase at 4°C. % |
|---|---|---|---|---|---|---|---|
| | | | After Preparation[a] | After 6 months at 4° C. | at 25° C. | at 50° C. | |
| 5 | 2.5 | 0 | 0.20 | 0.22 | 0.41 | 0.98 | 10 |
| 6 | 0.5 | | | | | | |
| Ref. | 0 | 3 | 100  0.3 | 0.65 | 0.65 | 1.5 | 117 |

[a]Emulsions prepared by microfluidization.

Additional stable perfluorodecalin (50% w/v) emulsions based on the perfluoroalkylated phosphatidylcholines 11 or 12 (2 or 3% w/v) as the sole surfactant have been prepared by sonication. It is noteworthy that the increase in average particle size was found to be smaller for the emulsions based on the F-alkylated surfactants (10% of increase) than for the reference emulsions (40% of increase) when prepared in similar conditions.

TABLE III

| Compound Number | EYP % (w/v) | F-decalin % (w/v) | Average Particle Size (µm) | | Relative Increase % |
|---|---|---|---|---|---|
| | | | After Preparation[a] | After 1 month | |
| 3 | 1 | 2 | 0.26 | 0.39[b] | 50 |
| 4 | 1 | 2 | 0.26 | 0.39[b] | 50 |
| 5 | 1 | 2 | 20  0.15 | 0.29[b] | 100 |
| 6 | 1 | 2 | 0.17 | 0.36[b] | 110 |
| Ref. | 0 | 3 | 0.15 | 0.44[b] | 200 |
| 11 | 0.66 | 1.33 | 0.37 | 0.50[c] | 35 |
| Ref. | 0 | 2 | 50  0.35 | 0.62[c] | 80 |

[a]Emulsions prepared by sonication
[b]The emulsions are stored at 25° C.
[c]The emulsions are stored at 50° C.

TABLE IV

| Compound Number | EYP % (w/v) | F-decalin % (w/v) | Average Particle size[a] (µm) | | | Relative increase % |
|---|---|---|---|---|---|---|
| | | | After preparation[a] | After 3 months | After 8 months | |
| 5 | 0.66 | 1.33 | 100  0.6 | 1.1 | 1.35 | 125 |
| Ref. | 0 | 2 | 100  0.49 | broken | | |

[a]All the emulsions are prepared by microfluidization and stored at 50° C.

The new perfluoroalkylated surfactants were solubilized or dispersed into water. Then the fluorocarbon was added under agitation. Any emulsification method like sonication can be used but mechanical procedures such as microfluidization or high pressure homogenization are preferred. The emulsion obtained can be used as an $O_2$ carrier. The significant stabilization effect which can be obtained by incorporating the new F-alkyl surfactants is illustrated for various emulsion formulations (see Tables above). The results show that both the average particle sizes, measured immediately after preparation, and stability (evaluated by the relative increase of the average particle sizes, for 1 to 6 months storage at 4, 25 and 50° C.) are always higher for the reference emulsions prepared with the same amount of natural EYP than for the F-alkyl-based one.

These experiments led to several important observations: simply the fact that it is possible to prepare 50% w/v F-decalin emulsions with F-alkylated amphiphiles as the sole surfactants, and that these emulsions are stable is by itself, remarkable (see Table I). It is also remarkable that it proved possible to prepare such 50% F-decalin emulsions, which remain stable at 50° C. for at least one month, with only 1% of 5. In comparison, when the same formulation is used, but with EYP instead of 5, phase separation is observed immediately (see Table I).

Another striking observation concerns the fact that at 4° C. there is no detectable change in particle size in the fluorinated surfactant 5 and 6-containing highly concentrated (100% w/v) F-decalin emulsion over a 6-month period of time (see Table II).

There will be various modifications, improvements, and applications of the disclosed invention that will be apparent to those of skill in the art, and the present application is intended to cover such embodiments. Although the present invention has been described in the context of certain preferred embodiments, it is intended that the full scope of the invention be measured by reference to the scope of the following claims.

What is claimed is:

1. A compound of the general formula:

$$\begin{array}{c} R^1-CH_2 \\ | \\ (R^2-CH)_m \quad O \\ | \quad \quad \| \\ CH_2-O-P-X \\ | \\ Y \end{array} \quad (Ia)$$

or $$\begin{array}{c} R^1-CH_2 \quad O \\ | \quad \quad \| \\ CH-O-P-X \\ | \quad \quad | \\ R^2-CH_2 \quad Y \end{array} \quad (Ib)$$

wherein:
m is 0 or 1;
$R^1$ represents:
$R_F(CH_2)_a-(CH=CH)_b-(CH_2)_c-(CH=CH)_d-(CH_2)_e-A-$;
$R_F-(CH_2)_f-OCH_2CH(CH_2OH)CH_2-A-$;
$R_F-(CH_2)_g-OCH_2CH(CH_2OH)-A-$;
  wherein —A— represents —O—, —C(O)O—, —$R^6(R^7)N^+$—, (wherein each of $R^6$ and $R^7$ represents $C_1$-$C_4$ alkyl or hydroxyethyl), —$(CH_2)_n$—, wherein n=0 or 1, or —C(O)N($R^9$)—$(CH_2)_q$—B, wherein q is an integer from 0 to 12, B represents —O— or —C(O)—, and $R^9$ is hydrogen or $R^6$, and wherein the sum of a+c+e is from 0 to 11, the sum b+d is from 0 to 12 and each of f and g is from 1 to 12;

$R_F-(CH_2-CH_2-O)_h-$;
$R_F-(CH(CH_3)CH_2O)_h-$; or
$R_F-(CH_2-CH_2-S)_h-$,
wherein h is from 1 to 12; and
wherein $R_F$ represents a fluorine-containing moiety having one of the following structures:
(a) $F(CF_2)_i-$, wherein i is from 2 to 12,
(b) $(CF_3)_2CF(CF_3)_j-$, wherein j is from 0 to 8,
(c) $R_F1(CF_2CF(CF_3))_k-$, wherein k is from 1 to 4, and $R_F1$ represents $CF_3-$, $C_2F_5-$ or $(CF_3)_2CF-$,
(d) $R_F2(R_F3)CFO(CF_2CF_2)_l-$, wherein l is from 1 to 6 and wherein each of $R_F2$ and $R_F3$ independently represents $CF_3-$, $C_2F_5-$, n-$C_3F_7-$ or $CF_3CF_2CF(CF_3)-$ or $R_F2$ and $R_F3$ taken together represent —$(CF_2)_4-$ or —$(CF_2)_5-$, provided that in compounds of the general formula Ia, when m=0, $R^1$ is $R_F(CH_2)_a-(CH=CH)_b-(CH_2)_c-(CH=CH)_d-(CH_2)_e-A-$, wherein —A— is —$(CH_2)_n-$ and n=0, each of $R_F2$ and $R_F3$ represents $CF_3-$, and l is 1, then the sum of b+d must be 1 or more; or
(e) one of the structures (a) to (d) in which one or more of the fluorine atoms are replaced by one or more hydrogen or bromine atoms and/or at least two chlorine atoms in a proportion such that at least 50% of the atoms bonded to the carbon skeleton of $R_F$ are fluorine atoms, and wherein $R_F$ contains at least 4 fluorine atoms, $R^2$ represents $R^1$, hydrogen or a group OR,
  wherein R represents a saturated or unsaturated $C_1$-$C_{20}$ alkyl or $C_4$-$C_{20}$ acyl; and
when m is 1, $R^1$ and $R^2$ may exchange their positions; and
each of X and Y independently represent:
hydroxyl;
—$OCH_2CH(OH)CH_2OH$;
—$O(CH_2CH_2O)_nR^3$,
  wherein n is an integer from 1 to 5; and
  $R^3$ represents a hydrogen atom or $C_1$-$C_4$ alkyl group;
—$NR^4R^5$ or $N^+R^4R^5R^8$,
  wherein each of $R^4$, $R^5$ and $R^8$ independently represents a hydrogen atom; a $C_1$-$C_4$ alkyl group;
—$CH_2CH_2O(CH_2CH_2O)_sR^3$, wherein s represents an integer of from 1 to 5, or $R^4$ and $R^5$ when taken together represent —$(CH_2)_q$ wherein q is an integer of from 2 to 5, or when with the nitrogen atom $R^4$ and $R^5$ form a morpholino group;
—$O(CH_2)_pZ$ wherein Z represents a 2-aminoacetic acid group, —$NR^4R^5$ or —$N^+R^4R^5R^8$ where $R^8$ is as defined for $R^4$ and $R^5$ above and p is an integer of from 1 to 5;
with the proviso that X and Y do not both represent hydroxyl; further provided for compounds of the general formula Ia, that when m=0 or 1, $R^2$ is H, and $R^1$ is $R_F(CH_2)_a-(CH=CH)_b-(CH_2)_c-(CH=CH)_d-A-$, in which A is $CH_2$ or O; or, when m=0 and $R^1$ is $R_F-CH_2-CH_2-O)_h$, one of X and Y is not $CH_2CH(OH)CH_2OH$ when the other is OH or an ionized form derived from OH.

2. A compound of the general formula:

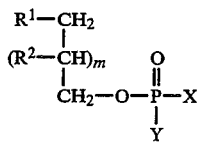

(Ia)

or

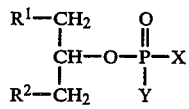

(Ib)

wherein:
m=0;
R¹ represents:
  $R_F$—(CH₂)$_a$—(CH=CH)$_b$—(CH₂)$_c$—(CH=CH)$_d$—(CH₂)$_e$—A—;
  $R_F$—(CH₂)$_f$—OCH₂CH(CH₂OH)CH₂—A—;
  $R_F$—(CH₂)$_g$—OCH₂CH(CH₂OH)—A—;
    wherein —A— represents —O—, —C(O)O—, —R⁶(R⁷)N⁺—, (wherein each of R⁶ and R⁷ represents C₁-C₄ alkyl or hydroxyethyl), —(CH₂)$_n$—, wherein n=0 or 1, or —C(O)N(R⁹)—(CH₂)$_q$—B,
  wherein q is an integer from 0 to 12;
  B represents —O— or —C(O)—, and R⁹ is hydrogen or R⁶; and wherein the sum of a+c+e is from 0 to 11, the sum b+d is from 0 to 12 and each of f and g is from 1 to 12;
  $R_F$—(CH₂—CH₂—O)$_h$—;
  $R_F$—(CH(CH₃)CH₂O)$_h$—; or
  $R_F$(—CH₂—CH₂—S)$_h$—,
    wherein h is from 1 to 12; and
  wherein $R_F$ is F(CF₂)$_i$—, wherein i is from 2 to 12;
R² represents R¹, hydrogen or a group OR,
  wherein R represents a saturated or unsaturated C₁-C₂₀ alkyl or C₄-C₂₀ acyl; and
each of X and Y independently represent:
  hydroxyl;
  —OCH₂CH(OH)CH₂OH;
  —O(CH₂CH₂O)$_n$R³,
    wherein n is an integer from 1 to 5; and
    R³ represents a hydrogen atom or C₁-C₄ alkyl group; —NR⁴R⁵ or N⁺R⁴R⁵R⁸,
    wherein each of R⁴, R⁵ and R⁸ independently represents a hydrogen atom; a C₁-C₄ alkyl group;
  —CH₂CH₂O(CH₂CH₂O)$_s$R³, wherein s represents an integer of from 1 to 5, or R⁴ and R⁵ when taken together represent —(CH₂)$_q$ wherein q is an integer of from 2 to 5, or when with the nitrogen atom R⁴ and R⁵ form a morpholino group;
  —O(CH₂)$_p$Z wherein Z represents a 2-aminoacetic acid group, —NR⁴R⁵ or —N⁺R⁴R⁵R⁸ where R⁸ is as defined for R⁴ and R⁵ above, and p is an integer of from 1 to 5;
with the proviso that X and Y do not both represent hydroxyl; and further provided for compounds of the general formula Ia, that when R² is H, and R¹ is $R_F$(CH₂)$_a$—(CH=CH)$_b$—(CH₂)$_c$—(CH=CH)$_d$—A—, in which A is CH₂ or O; or, when R¹ is $R_F$—CH₂—CH₂—O)$_h$, one of X and Y is not CH₂CH(OH)CH₂OH when the other is OH or an ionized form derived from OH.

3. The compound of claim 1, wherein $R_F$ is F(CF₂)$_i$ and m is 1.

4. A compound of the general formula:

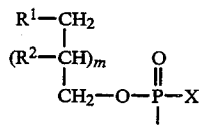

(Ia)

or

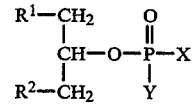

(Ib)

wherein:
m=1;
R¹ and R² each represents:
  $R_F$(CH₂)$_a$—(CH=CH)$_b$—(CH₂)$_c$—(CH=CH)$_d$—(CH₂)$_e$—A—;
  $R_F$—(CH₂)$_f$—OCH₂CH(CH₂OH)CH₂—A—;
  $R_F$—(CH₂)$_g$—OCH₂CH(CH₂OH)—A—;
    wherein —A— represents —O—, —C(O)O—, —R⁶(R⁷)N⁺—, (wherein each of R⁶ and R⁷ represents C₁-C₄ alkyl or hydroxyethyl), —(CH₂)$_n$—, wherein n=0 or 1, or —C(O)N(R⁹)—(CH₂)$_q$—B, wherein q is an integer from 0 to 12, B represents —O— or —C(O)—, and R⁹ is hydrogen or R⁶,
    and wherein the sum of a+c+e is from 0 to 11, the sum b+d is from 0 to 12 and each of f and g is from 1 to 12;
  $R_F$—(CH₂—CH₂—O)$_h$—;
  $R_F$—(CH(CH₃)CH₂O)$_h$—;
  $R_F$(—CH₂—CH₂—S)$_h$—,
    wherein h is from 1 to 12; and
  wherein $R_F$ represents F(CF₂)$_i$—, wherein i is from 2 to 12; and R² is the same as R¹; and
each of X and Y independently represent:
  hydroxyl;
  —OCH₂CH(OH)CH₂OH;
  —O(CH₂CH₂O)$_n$R³,
    wherein n is an integer from 1 to 5; and
    R³ represents a hydrogen atom or C₁-C₄ alkyl group; —NR⁴R⁵ or N⁺R⁴R⁵R⁸,
    wherein each of R⁴, R⁵ and R⁸ independently represents a hydrogen atom; a C₁-C₄ alkyl group;
  —CH₂CH₂O(CH₂CH₂O)$_s$R³, wherein s represents an integer of from 1 to 5, or R⁴ and R⁵ when taken together represent —(CH₂)$_q$ wherein q is an integer of from 2 to 5, or when with the nitrogen atom R⁴ and R⁵ form a morpholino group;
  —O(CH₂)$_p$Z wherein Z represents a 2-aminoacetic acid group, —NR⁴R⁵ or —N⁺R⁴R⁵R⁸ where R⁸ is as defined for R⁴ and R⁵ above, and p is an integer of from 1 to 5;
with the proviso that X and Y do not both represent hydroxyl; and further provided for compounds of the general formula Ia, that when R² is H, and R¹ is $R_F$(CH₂)$_a$—(CH=CH)$_b$—(CH₂)$_c$—(CH=CH)$_d$—A—, in which A is CH₂ or O; one of X and Y is not CH₂CH(OH)CH₂OH when the other is OH or an ionized form derived from OH.

5. A compound of any one of claims 1 to 4, wherein $R^1$ is $R_F$ $(CH_2)_a$—$(CH=CH)_b$—$(CH_2)_c$—$(CH=CH)_d$—$(CH_2)_e$—A—.

6. A compound of claim 5, wherein b+d=0.

7. A compound of claim 5, wherein A represents —O—, —C(O)O—, or —(CH₂)ₙ—, wherein n=0 or 1.

8. A compound of any one of claims 1 and 4, wherein $R_F$ is $F(CF_2)_i$—, and wherein i is from 2 to 12.

9. A compound of claim 8, wherein i is from 4 to 8.

10. A compound of the general formula:

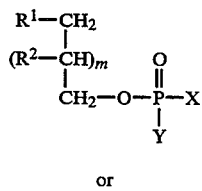  (Ia)

or

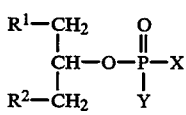  (Ib)

wherein:
m=0 or 1;
$R^1$ represents:
$R^1$ $(CH_2)_a$—$(CH=CH)_b$—$(CH_2)_c$—$(CH=CH)_d$—$(CH_2)_e$—A—;
$R_F$—$(CH_2)_f$—$OCH_2CH(CH_2OH)CH_2$—A—;
$R_F$—$(CH_2)_g$—$OCH_2CH(CH_2OH)$—A—;
wherein —A— represents —O—, —C(O)O—, —$R^6(R^7)N^+$—, (wherein each of $R^6$ and $R^7$ represents $C_1$-$C_4$ alkyl or hydroxyethyl),
(CH₂)ₙ—, wherein n=0 or 1, or
—C(O)N($R^9$)—$(CH_2)_q$—B, wherein q is an integer from 0 to 12, B represents —O— or —C(O)—, and $R^9$ is hydrogen or $R^6$,
and wherein the sum of a+c+e is from 0 to 11, the sum b+d is from 0 to 12 and each of f and g is from 1 to 12;
$R_F$—$(CH_2$—$CH_2$—$O)_h$—;
$R_F$—$(CH(CH_3)CH_2O)_h$—; or
$R_F$(—$CH_2$—$CH_2$—$S)_h$—,
wherein h is from 1 to 12; and
wherein $R_F$ represents a fluorine-containing moiety having one of the following structures:
(a) F $(CF_2)_i$—, wherein i is from 2 to 12,
(b) $(CF_3)_2CF(CF_2)_j$—, wherein j is from 0 to 8,
(c) $R_{F1}(CF_2CF(CF_3))_k$—, wherein k is from 1 to 4, and $R_{F1}$ represents $CF_3$—, $C_2F_5$— or $(CF_3)_2CF$—,
(d) $R_{F2}(R_{F3})CFO(CF_2CF_2)_l$—, wherein l is from 1 to 6 and wherein each of $R_{F2}$ and $R_{F3}$ independently represents $CF_3$—, $C_2F_5$—, n—$C_3F_7$— or $CF_3CF_2CF(CF_3)$— or $R_{F2}$ and $R_{F3}$ taken together represent —$(CF_2)_4$— or —$(CF_2)_5$—, provided that in compounds of the general formula of Ia, when m=0, $R^2$ is H, $R^1$ is $R_F(CH_2)_a$—$(CH=CH)_b$—$(CH_2)_c$—$(CH=CH)_d$—$(CH_2)_e$—A—, wherein —A— is —$(CH_2)_n$— and n=0, each of $R_{F2}$ and $R_{F3}$ represents $CF_3$—, and l=1, then the sum of b+d must be 1 or more; or (e) one of the structures (a) to (d) in which one or more of the fluorine atoms are replaced by one or more hydrogen or bromine atoms and/or at least two chlorine atoms in a proportion such that at least 50% of the atoms bonded to the carbon skeleton of $R_F$ are fluorine atoms, and wherein $R^F$ contains at least 4 fluorine atoms;

$R^2$ represents $R^1$, hydrogen or a group OR,
wherein R represents a saturated or unsaturated $C_1$-$C_{20}$ alkyl or $C_4$-$C_{20}$ acyl; and
when m is 1, $R^1$ and $R^2$ may exchange their positions; and
each of X and Y independently represent:
hydroxyl, morpholino, or —$O(CH_2CH_2O)_nR^3$, wherein n is an integer 1 or 2; and
$R^3$ represents a methyl group, $CH_3$;
with the proviso that X and Y do not both represent hydroxyl or an ionized form derived from hydroxyl; and further provided for compounds of the general formula Ia, that when m=0 or 1, $R^2$ is H, and $R^1$ is $R_F(CH_2)_a$—$(CH=CH)_b$—$(CH_2)_c$—$(CH=CH)_d$—A—, in which A is CH₂ or O; or, when m=0 and $R^1$ is $R_F$—$CH_2$—$CH_2$—$O)_h$, one of X and Y is not CH₂CH(OH)CH₂OH when the other is OH or an ionized form derived from OH.

11. A compound of any one of claims 1 to 4, wherein at least one of X and Y represents —$OCH_2CH_2N^+(CH_3)_3$.

12. A compound having the general structure

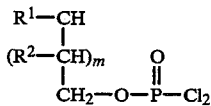 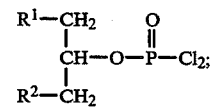

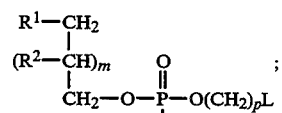 ; or 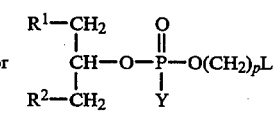

wherein L is Z or a leaving group selected from the group consisting of chlorine, bromine, iodine, or tosylate; and $R^1$, $R^2$, Y, Z, m, and p are as defined in claim 1.

13. A compound of any one of claims 2 and 3, wherein i is from 4 to 8.

* * * * *

UNITED STATES PATENT AND TRADEMARK OFFICE
CERTIFICATE OF CORRECTION

PATENT NO. : 5,344,930
DATED : September 6, 1994
INVENTOR(S) : Riess, et. al.

It is certified that error appears in the above-indentified patent and that said Letters Patent is hereby corrected as shown below:

On the Title page, item [30] insert Foreign Application Priority Data —

(30) June 22, 1989    European    89401 777 —.

Column 18, Line 13 change "$(CF_3)_j$" to --$(CF_2)_j$--.

Column 19, Line 33 change "$(CH_2-CH_2-O)_1$" to --$(CH_2-CH_2-O)_h$--.

Column 19, Line 47 change "$N+R^4R_5R^8$" to --$N+R^4R^5R^8$--.

Signed and Sealed this

Ninth Day of May, 1995

Attest:

BRUCE LEHMAN

*Attesting Officer*    *Commissioner of Patents and Trademarks*